US012682260B2

(12) United States Patent
Cheng et al.

(10) Patent No.: US 12,682,260 B2
(45) Date of Patent: Jul. 14, 2026

(54) ADJUDICATION ALGORITHM BYPASS CONDITIONS

(71) Applicant: Medtronic, Inc., Minneapolis, MN (US)

(72) Inventors: Ya-Jian Cheng, Lino Lakes, MN (US); Sean R. Landman, Minneapolis, MN (US); Bruce D. Gunderson, Plymouth, MN (US); Paul D. Ziegler, Cable, WI (US); Shantanu Sarkar, Roseville, MN (US); Kevin T. Ousdigian, Shoreview, MN (US); Gautham Rajagopal, Minneapolis, MN (US); Ekaterina M. Ippolito, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 954 days.

(21) Appl. No.: 17/804,259

(22) Filed: May 26, 2022

(65) Prior Publication Data

US 2022/0398470 A1 Dec. 15, 2022

Related U.S. Application Data

(60) Provisional application No. 63/210,923, filed on Jun. 15, 2021.

(51) Int. Cl.
*G06N 5/04* (2023.01)
*G16H 40/67* (2018.01)

(52) U.S. Cl.
CPC .............. *G06N 5/04* (2013.01); *G16H 40/67* (2018.01)

(58) Field of Classification Search
CPC ................................... G06N 5/02; G06N 5/04

USPC ...................................................... 706/52, 46
See application file for complete search history.

(56) References Cited

U.S. PATENT DOCUMENTS

| | | | |
|---|---|---|---|
| 4,291,699 A | 9/1981 | Geddes et al. | |
| 4,428,378 A | 1/1984 | Anderson et al. | |
| 5,052,388 A | 10/1991 | Sivula et al. | |
| 5,117,824 A | 6/1992 | Keimel et al. | |

(Continued)

FOREIGN PATENT DOCUMENTS

| | | |
|---|---|---|
| CN | 110916647 A | 3/2020 |
| EP | 2217140 A1 | 8/2010 |

(Continued)

OTHER PUBLICATIONS

"Causes of Hypoperfusion state," Right Diagnosis, last updated Aug. 13, 2015, accessed from http://www.rightdiagnosis.com/symptoms/hypoperfusion_state/causes.htm, 2 pp.

(Continued)

*Primary Examiner* — Hwei-Min Lu
(74) *Attorney, Agent, or Firm* — Shumaker & Sieffert, P.A.

(57) ABSTRACT

This disclosure describes techniques for bypassing an algorithm configured to determine a likelihood of episode data being a false indication of a cardiac episode. A medical device system includes processing circuitry configured to receive episode data and determine, based on satisfaction of one or more bypass conditions of a set of bypass conditions, whether to bypass the algorithm. Responsive to bypassing the algorithm, the processing circuitry stores the episode data as a true indication of the cardiac episode.

20 Claims, 5 Drawing Sheets

(56)     References Cited

U.S. PATENT DOCUMENTS

| | | | |
|---|---|---|---|
| 5,335,668 A | 8/1994 | Nardella | |
| 5,368,040 A | 11/1994 | Carney | |
| 5,536,267 A | 7/1996 | Edwards et al. | |
| 5,788,643 A | 8/1998 | Feldman | |
| 5,792,204 A | 8/1998 | Snell | |
| 5,857,975 A | 1/1999 | Golub | |
| 6,024,704 A | 2/2000 | Meador et al. | |
| 6,336,903 B1 | 1/2002 | Bardy | |
| 6,409,675 B1 | 6/2002 | Turcott | |
| 6,480,733 B1 | 11/2002 | Turcott | |
| 6,546,935 B2 | 4/2003 | Hooven | |
| 6,714,806 B2 | 3/2004 | Iaizzo et al. | |
| 6,980,675 B2 | 12/2005 | Evron et al. | |
| 7,029,447 B2 | 4/2006 | Rantala | |
| 7,286,866 B2 | 10/2007 | Okerlund et al. | |
| 7,308,297 B2 | 12/2007 | Reddy et al. | |
| 7,308,299 B2 | 12/2007 | Burrell et al. | |
| 7,321,677 B2 | 1/2008 | Evron et al. | |
| 7,346,381 B2 | 3/2008 | Okerlund et al. | |
| 7,454,248 B2 | 11/2008 | Burrell et al. | |
| 7,460,909 B1 | 12/2008 | Koh et al. | |
| 7,499,743 B2 | 3/2009 | Vass et al. | |
| 7,558,622 B2 | 7/2009 | Tran | |
| 7,565,190 B2 | 7/2009 | Okerlund et al. | |
| 7,587,074 B2 | 9/2009 | Zarkh et al. | |
| 7,599,730 B2 | 10/2009 | Hunter et al. | |
| 7,605,865 B2 | 10/2009 | Lin | |
| 7,613,500 B2 | 11/2009 | Vass et al. | |
| 7,684,863 B2 | 3/2010 | Parikh et al. | |
| 7,706,865 B1 | 4/2010 | Snell | |
| 7,742,629 B2 | 6/2010 | Zarkh et al. | |
| 7,747,047 B2 | 6/2010 | Okerlund et al. | |
| 7,778,685 B2 | 8/2010 | Evron et al. | |
| 7,778,686 B2 | 8/2010 | Vass et al. | |
| 7,813,785 B2 | 10/2010 | Okerlund et al. | |
| 7,983,744 B2 | 7/2011 | Ricci et al. | |
| 7,991,484 B1 | 8/2011 | Sengupta et al. | |
| 7,996,063 B2 | 8/2011 | Vass et al. | |
| 8,060,185 B2 | 11/2011 | Hunter et al. | |
| 8,062,227 B2 | 11/2011 | Cho et al. | |
| 8,180,428 B2 | 5/2012 | Kaiser et al. | |
| 8,180,454 B2 | 5/2012 | Greenberg et al. | |
| 8,323,189 B2 | 12/2012 | Tran et al. | |
| 8,346,332 B2 | 1/2013 | Kuhn et al. | |
| 8,380,303 B2 | 2/2013 | Rosenberg et al. | |
| 8,401,616 B2 | 3/2013 | Verard et al. | |
| 8,475,370 B2 | 7/2013 | McCombie et al. | |
| 8,491,485 B2 | 7/2013 | Czygan et al. | |
| 8,494,829 B2 | 7/2013 | Teixeira | |
| 8,515,537 B2 | 8/2013 | Cinbis et al. | |
| 8,521,269 B1* | 8/2013 | Gunderson | A61N 1/37247 |
| | | | 600/518 |
| 8,521,281 B2 | 8/2013 | Patel et al. | |
| 8,708,924 B2 | 4/2014 | Wariar et al. | |
| 8,744,572 B1 | 6/2014 | Greenhut et al. | |
| 8,768,718 B2 | 7/2014 | Cazares et al. | |
| 8,812,102 B2 | 8/2014 | Li et al. | |
| 8,821,404 B2 | 9/2014 | Thakur et al. | |
| 8,886,296 B2 | 11/2014 | Patel | |
| 8,977,350 B2 | 3/2015 | Sarkar et al. | |
| 9,174,054 B1 | 11/2015 | Nabutovsky et al. | |
| 9,199,086 B2 | 12/2015 | Zielinski et al. | |
| 9,320,446 B2 | 4/2016 | Gillberg et al. | |
| 9,474,457 B2 | 10/2016 | Ghosh et al. | |
| 9,486,151 B2 | 11/2016 | Ghosh et al. | |
| 9,662,073 B2 | 5/2017 | Zhang et al. | |
| 9,669,218 B2 | 6/2017 | Libbus et al. | |
| 9,717,438 B2 | 8/2017 | Bayasi et al. | |
| 9,826,939 B2 | 11/2017 | Averina et al. | |
| 9,901,276 B2 | 2/2018 | Sarkar | |
| 9,907,959 B2 | 3/2018 | Skelton | |
| 9,936,890 B2 | 4/2018 | Sarkar et al. | |
| 10,143,839 B1 | 12/2018 | Christie et al. | |
| 10,182,729 B2 | 1/2019 | Zielinski et al. | |
| 10,252,068 B2 | 4/2019 | Gunderson et al. | |
| 10,265,028 B2 | 4/2019 | Moturu et al. | |
| 10,595,731 B2 | 3/2020 | Gopalakrishnan et al. | |
| 10,610,111 B1 | 4/2020 | Tran | |
| 10,610,132 B2 | 4/2020 | Gunderson et al. | |
| 10,850,113 B2 | 12/2020 | Cao et al. | |
| 10,898,720 B2 | 1/2021 | Christie et al. | |
| 11,071,500 B2 | 7/2021 | Cheng et al. | |
| 11,375,905 B2 | 7/2022 | Gunderson et al. | |
| 2002/0058969 A1 | 5/2002 | Noren et al. | |
| 2003/0199938 A1 | 10/2003 | Smits et al. | |
| 2004/0049120 A1 | 3/2004 | Cao et al. | |
| 2004/0092836 A1* | 5/2004 | Ritscher | A61N 1/3622 |
| | | | 600/518 |
| 2004/0133113 A1 | 7/2004 | Krishnan | |
| 2004/0204734 A1 | 10/2004 | Wagner et al. | |
| 2005/0008210 A1 | 1/2005 | Evron et al. | |
| 2006/0041281 A1 | 2/2006 | Von Arx et al. | |
| 2006/0069419 A1 | 3/2006 | Sweeney et al. | |
| 2006/0074285 A1 | 4/2006 | Zarkh et al. | |
| 2007/0043394 A1 | 2/2007 | Zhang et al. | |
| 2007/0115277 A1 | 5/2007 | Wang et al. | |
| 2007/0129765 A1 | 6/2007 | Gilkerson et al. | |
| 2007/0260285 A1 | 11/2007 | Libbus et al. | |
| 2008/0004667 A1 | 1/2008 | Arcot-Krishnamurthy et al. | |
| 2008/0065061 A1 | 3/2008 | Viswanathan | |
| 2008/0065165 A1* | 3/2008 | Johnson | A61B 5/7264 |
| | | | 607/27 |
| 2008/0183083 A1 | 7/2008 | Markowitz et al. | |
| 2008/0228090 A1 | 9/2008 | Wariar et al. | |
| 2008/0269813 A1 | 10/2008 | Greenhut | |
| 2009/0062667 A1 | 3/2009 | Fayram et al. | |
| 2009/0063193 A1 | 3/2009 | Barton et al. | |
| 2009/0099619 A1 | 4/2009 | Lessmeier et al. | |
| 2009/0281399 A1 | 11/2009 | Keel et al. | |
| 2009/0299422 A1 | 12/2009 | Ousdigian et al. | |
| 2009/0326350 A1 | 12/2009 | Kracker | |
| 2010/0010338 A1 | 1/2010 | van Dam et al. | |
| 2010/0041970 A1 | 2/2010 | Hedberg et al. | |
| 2010/0113944 A1 | 5/2010 | Min et al. | |
| 2010/0113963 A1 | 5/2010 | Smits et al. | |
| 2010/0179411 A1 | 7/2010 | Holmström et al. | |
| 2010/0241180 A1* | 9/2010 | Whitman | A61B 5/363 |
| | | | 607/18 |
| 2010/0274219 A1 | 10/2010 | Wenzel et al. | |
| 2010/0312131 A1* | 12/2010 | Naware | A61B 5/287 |
| | | | 600/518 |
| 2011/0009754 A1 | 1/2011 | Wenzel et al. | |
| 2011/0066203 A1 | 3/2011 | Rosenberg et al. | |
| 2011/0098771 A1 | 4/2011 | Thakur et al. | |
| 2011/0105932 A1 | 5/2011 | Bauer et al. | |
| 2011/0112398 A1 | 5/2011 | Zarkh et al. | |
| 2011/0112597 A1* | 5/2011 | Snell | A61N 1/37235 |
| | | | 607/27 |
| 2011/0125049 A1 | 5/2011 | Nabutovsky et al. | |
| 2011/0172504 A1 | 7/2011 | Wegerich | |
| 2011/0184297 A1 | 7/2011 | Vitali et al. | |
| 2011/0190654 A1 | 8/2011 | Hettrick et al. | |
| 2011/0196247 A1 | 8/2011 | Cao et al. | |
| 2011/0224498 A1 | 9/2011 | Banet et al. | |
| 2011/0230771 A1 | 9/2011 | Koh et al. | |
| 2011/0245698 A1 | 10/2011 | Wang et al. | |
| 2011/0319777 A1 | 12/2011 | Mehrotra et al. | |
| 2012/0029373 A1 | 2/2012 | Stadler et al. | |
| 2012/0109243 A1 | 5/2012 | Hettrick et al. | |
| 2012/0133602 A1 | 5/2012 | Kamamoto et al. | |
| 2012/0283587 A1 | 11/2012 | Gosh et al. | |
| 2012/0284003 A1 | 11/2012 | Gosh et al. | |
| 2013/0096449 A1 | 4/2013 | Patel et al. | |
| 2013/0116578 A1 | 5/2013 | An et al. | |
| 2013/0116739 A1 | 5/2013 | Brada et al. | |
| 2013/0123617 A1 | 5/2013 | Caros et al. | |
| 2013/0179139 A1 | 7/2013 | Lee | |
| 2014/0195168 A1 | 7/2014 | Shaihk | |
| 2014/0221849 A1 | 8/2014 | Farringdon et al. | |
| 2014/0276928 A1 | 9/2014 | Vanderpool et al. | |
| 2014/0316429 A1 | 10/2014 | Smits et al. | |
| 2014/0323882 A1 | 10/2014 | Ghosh et al. | |
| 2014/0323892 A1 | 10/2014 | Ghosh et al. | |
| 2014/0330172 A1 | 11/2014 | Jovanov et al. | |

(56) References Cited

U.S. PATENT DOCUMENTS

| | | | |
|---|---|---|---|
| 2014/0343371 A1 | 11/2014 | Sowers, II et al. | |
| 2014/0371832 A1 | 12/2014 | Ghosh et al. | |
| 2014/0371833 A1 | 12/2014 | Ghosh et al. | |
| 2015/0157231 A1 | 6/2015 | Gillberg et al. | |
| 2015/0157232 A1 | 6/2015 | Gillberg et al. | |
| 2015/0157865 A1 | 6/2015 | Gillberg et al. | |
| 2015/0164437 A1 | 6/2015 | Mccombie et al. | |
| 2015/0283383 A1 | 10/2015 | Ternes et al. | |
| 2016/0030751 A1 | 2/2016 | Ghosh et al. | |
| 2016/0045737 A1 | 2/2016 | Ghosh et al. | |
| 2016/0045738 A1 | 2/2016 | Ghosh et al. | |
| 2016/0045744 A1 | 2/2016 | Gillberg et al. | |
| 2016/0081571 A1 | 3/2016 | Bauer | |
| 2016/0095555 A1 | 4/2016 | Stainer et al. | |
| 2016/0144192 A1 | 5/2016 | Sanghera et al. | |
| 2016/0256063 A1 | 9/2016 | Friedman et al. | |
| 2016/0256687 A1 | 9/2016 | Baru et al. | |
| 2016/0310031 A1 | 10/2016 | Sarkar | |
| 2016/0367194 A1 | 12/2016 | Murphy | |
| 2017/0086697 A1* | 3/2017 | Bellock | A61B 5/364 |
| 2017/0100056 A1 | 4/2017 | Zhu et al. | |
| 2017/0119263 A1 | 5/2017 | Hill | |
| 2017/0128734 A1* | 5/2017 | Gunderson | A61N 1/3925 |
| 2017/0143216 A1 | 5/2017 | Oksala et al. | |
| 2017/0156604 A1 | 6/2017 | Zhang et al. | |
| 2017/0209053 A1 | 7/2017 | Pantelopoulos et al. | |
| 2017/0231568 A1 | 8/2017 | An et al. | |
| 2017/0238812 A1 | 8/2017 | Atlas | |
| 2017/0265782 A1 | 9/2017 | Vollmer | |
| 2017/0273589 A1 | 9/2017 | Sarkar et al. | |
| 2017/0281024 A1 | 10/2017 | Narasimhan et al. | |
| 2017/0281095 A1 | 10/2017 | An et al. | |
| 2017/0340209 A1 | 11/2017 | Klaassen et al. | |
| 2017/0347969 A1 | 12/2017 | Thakur et al. | |
| 2018/0028083 A1 | 2/2018 | Greenhut et al. | |
| 2018/0028086 A1 | 2/2018 | Cao et al. | |
| 2018/0035898 A1 | 2/2018 | Gunderson | |
| 2018/0035920 A1 | 2/2018 | Gunderson et al. | |
| 2018/0035924 A1 | 2/2018 | Gunderson et al. | |
| 2018/0035956 A1 | 2/2018 | Gunderson et al. | |
| 2018/0055386 A1 | 3/2018 | Zielinski et al. | |
| 2018/0060520 A1 | 3/2018 | Degen et al. | |
| 2018/0116626 A1 | 5/2018 | Darbari et al. | |
| 2018/0177486 A1 | 6/2018 | Gifford, III et al. | |
| 2018/0264258 A1 | 9/2018 | Cheng et al. | |
| 2019/0043610 A1 | 2/2019 | Vaughan | |
| 2019/0133457 A1 | 5/2019 | Sun et al. | |
| 2019/0231207 A1* | 8/2019 | Perschbacher | A61B 5/0006 |
| 2019/0298272 A1 | 10/2019 | Persen et al. | |
| 2019/0329038 A1* | 10/2019 | Rhude | A61B 5/0024 |
| 2019/0336025 A1* | 11/2019 | Qu | A61B 5/361 |
| 2019/0336076 A1 | 11/2019 | Kuhn et al. | |
| 2019/0336077 A1 | 11/2019 | Kuhn et al. | |
| 2019/0343415 A1 | 11/2019 | Saha et al. | |
| 2019/0374123 A1 | 12/2019 | Bouguerra et al. | |
| 2020/0054292 A1 | 2/2020 | Govari et al. | |
| 2020/0100693 A1 | 4/2020 | Velo | |
| 2020/0178829 A1* | 6/2020 | Perschbacher | A61B 5/33 |
| 2020/0187866 A1 | 6/2020 | Antunes et al. | |
| 2020/0205745 A1 | 7/2020 | Khosousi et al. | |
| 2020/0289033 A1 | 9/2020 | Sivertsen et al. | |
| 2020/0323452 A1 | 10/2020 | Mahajan et al. | |
| 2020/0330020 A1 | 10/2020 | Rundo et al. | |
| 2020/0337580 A1 | 10/2020 | Oh et al. | |
| 2020/0345261 A1 | 11/2020 | Haeusser et al. | |
| 2020/0345309 A1 | 11/2020 | Cheng et al. | |
| 2020/0352441 A1 | 11/2020 | Soykan et al. | |
| 2020/0352466 A1 | 11/2020 | Chakravarthy et al. | |
| 2020/0352521 A1* | 11/2020 | Chakravarthy | A61B 5/363 |
| 2020/0357517 A1 | 11/2020 | Haddad et al. | |
| 2020/0357518 A1 | 11/2020 | Musgrove et al. | |
| 2021/0052175 A1* | 2/2021 | Stephens | A61B 5/721 |
| 2021/0127992 A1 | 5/2021 | Gunderson et al. | |
| 2021/0146141 A1 | 5/2021 | Christie et al. | |
| 2021/0236063 A1 | 8/2021 | Cheng et al. | |
| 2021/0272696 A1 | 9/2021 | DeMazumder | |
| 2021/0345969 A1 | 11/2021 | Cheng et al. | |
| 2022/0051091 A1 | 2/2022 | Ravuna et al. | |
| 2022/0215930 A1 | 7/2022 | Eshel et al. | |
| 2022/0322952 A1 | 10/2022 | Gunderson et al. | |
| 2022/0401037 A1 | 12/2022 | Sadeghzadeh et al. | |
| 2023/0034970 A1 | 2/2023 | Cheng et al. | |
| 2023/0309839 A1* | 10/2023 | Attar | A61B 5/02028 600/508 |

FOREIGN PATENT DOCUMENTS

| | | | |
|---|---|---|---|
| EP | 2371280 | B1 | 10/2011 |
| EP | 4008241 | A1 | 6/2022 |
| WO | 2009072034 | A1 | 6/2009 |
| WO | 2013054242 | A1 | 4/2013 |
| WO | 2015048514 | A1 | 4/2015 |
| WO | 2016061381 | A1 | 4/2016 |
| WO | 2020227514 | A1 | 11/2020 |

OTHER PUBLICATIONS

"VCSEL-ULM763-SingleMODE_TO5_v13," Philips, accessed on Nov. 7, 2017, accessed from http://www.photonics.philips.com/pdf/VCSEL-ULM763-SingleMode_TO5.pdf, 2 pp.

Abay et al., "Reflectance Photoplethysmography as Noninvasive Monitoring of Tissue Blood Perfusion," IEEE Transactions on Biomedical Engineering, vol. 62, No. 9, Sep. 2015, pp. 2187-2195.

Alam et al., "A dynamic ensemble learning algorithm for neural networks", Neural Computing and Applications, Jul. 29, 2019, 16 pp.

Alfaras et al., "A Fast Machine Learning Model for ECG-Based Heartbeat Classification and Arrhythmia Detection", frontiers in Physics, Jul. 18, 2019, 11 pp.

Auricchio et al., "Reducing Ventricular Pacing Frequency in Patients with Atrioventricular Block", Advances in Arrhythmia and Electrophysiology, vol. 9, No. 9, American Heart Association, Sep. 16, 2016, p. 10.

Bennett et al., "Development of Implantable Devices for Continuous Ambulatory Monitoring of Central Hemodynamic Values in Heart Failure Patients," Pace, vol. 28, Jun. 2005, pp. 573-584.

Bereski-Reguig et al., "A New System for Measurement of the Pulse Transit Time, the Pulse Wave Velocity and its Analysis", World Scientific, Journal of Mechanics in Medicine and Biology, vol. 17, No. 1, Apr. 2016, 21 pp.

Bernard, M.L., "Pacing Without Wires: Leadless Cardiac Pacing," The Ochsner Journal, vol. 16, No. 3, Oct. 2016, 5 pp.

Burkland et al., "Near-Field Impedance Accurately Distinguishes Among Pericardial, Intracavitary, and Anterior Mediastinal Position", Journal of Cardiovascular Electrophysiology, Jun. 2017, 10 pages.

Charach et al., "Internal Thoracic Impedance—A Useful Method for Expedient Detection and Convenient Monitoring of Pleural Effusion," PLOS ONE, published Apr. 28, 2015, 14 pp.

Chen, "Deep and Modular Neural Networks", Springer Handbook of Computational Intelligence 2015. (Applicant points out, in accordance with MPEP 609.04(a), that the year of publication, 2015, is sufficiently earlier than the effective U.S. filing date, so that the particular month of publication is not in issue.) 33 pp.

Cowie et al., "Development and validation of an integrated diagnostic algorithm derived from parameters monitored in implantable devices for identifying patients at risk for heart failure hospitalization in an ambulatory setting," European Heart Journal; 43, published online Mar. 19, 2013, pp. 2472-2480.

Edlow et al., "The effects of healthy aging on cerebral hemodynamic responses to posture change," Physiological Measurement, vol. 31, No. 4, Feb. 2010, 19 pp.

Fiala et al., "Implantable Reflectance Pulse Transit Time Blood Pressure Sensor with Oximetry Capability," Proceedings SPIE 7513, 2009 International Conference on Optical Instruments and Technology, vol. 7715, Apr. 28, 2010, 6 pages.

(56)     References Cited

OTHER PUBLICATIONS

Fontaine et al., "Reflectance-Based Pulse Oximeter for the Chest and Wrist," A Major Qualifying Project Report. Worchester Polytechnic Institute, accessed on Nov. 7, 2017, 96 pp.

Forrester et al., "Correlative Classification of Clinical and Hemodynamic Function after Acute Myocardial Infarction," The American Journal of Cardiology, vol. 39, Issue 2, Feb. 1977, pp. 137-145.

Gholamhosseini et al., "Smartphone-based blood pressure monitoring for falls risk assessment: techniques and technologies," Human Monitoring, Smart Health and Assisted Living: Techniques and Technologies, May 31, 2017, pp. 203-215.

Hogan et al., "Quantitative tissue hemoglobin oxygen saturation measurement in decompensated heart failure," J. Cardiothoracic-Renal Research, May 2006, 1, 153-157.

Hogan et al., "The Utility of Microvascular Perfusion Assessment in Heart Failure: A Pilot Study," J. Cardiac Failure, vol. 11, No. 9, Jul. 2005, pp. 713-719.

Hsia et al., Novel Minimally Invasive, Intrapericardial Implantable Cardioverter Defibrillator Coil System: A Useful Approach to Arrhythmia Theraphy in Children, Ann Thorac Surg, Apr. 2009, vol. 87, 6 pages.

International Search Report and Written Opinion of International Application No. PCT/US2022/031234 dated Aug. 19, 2022, 9 pp.

Javadi et al., "Improving ECG Classification Accuracy Using an Ensemble of Neural Network Modules", Improving ECG Classification Accuracy Using an Ensemble of Neural Network Modules, Oct. 26, 2011, 13 pp.

Mathunjwa et al., "ECG arrhythmia classification by using a recurrence plot and convolutional neural network", Biomedical Signal Processing and Control, Oct. 4, 2020, 15 pp.

Myers et al., "Tissue hemoglobin index: a non-invasive optical measure of total tissue hemoglobin," Critical Care, vol. 13, Suppl. 5, Nov. 30, 2009, 13 pp.

Nohria, MD, et al. "Clinical Assessment Identifies Hemodynamic Profiles that Predict Outcomes in Patients Admitted with Heart Failures," J. Am. Col Cardiology, vol. 41, No. 10, May 21, 2003, 1797-1804.

Pandey et al., "Automatic detection of arrhythmia from imbalanced ECG database using CNN model with SMOTE", Australasian Physical & Engineering Sciences in Medicine (2019), Nov. 14, 2019, 11 pp.

Plawiak et al., "Novel deep genetic ensemble of classifiers for arrhythmia detection using ECG signals", Neural Computing and Applications, Jan. 5, 2019, 25 pp.

Podbregar et al., "Skeletal muscle oxygen saturation does not estimate mixed venous oxygen saturation in patients with severe left heart failure and additional severe sepsis or septic shock," Critical Care, Jan. 2007, 11: R6.

Ponikowski et al. "2016 ESC Guidelines for the diagnosis and treatment of acute and chronic heart failure," European Heart Journal, May 2016, 37, 2129-2200.

Ryu, et al., "Simultaneous Electrical and Mechanical Mapping Using 3d Cardiac Mapping System: Novel Approach for Optimal Cardiac Resynchronization Therapy," Journal of Cardiovascular Electrophysiology, Feb. 2010, vol. 21, No. 2, pp. 219-222. (4 pages).

Sarkar et al., "A Dynamic Risk Score to Identify Increased Risk for Heart Failure Decompensation," IEEE Transactions on Biomedical Engineering, vol. 60, No. 1, Jan. 2013, pp. 147-150.

Sevakula et al., "State-of-the-Art Machine Learning Techniques Aiming to Improve Patient Outcomes Pertaining to the Cardiovascular System", J Am Heart Assoc. 2020 (Applicant points out, in accordance with MPEP 609.04(a), that the year of publication, 2020, is sufficiently earlier than the effective U.S. filing date, so that the particular month of publication is not in issue.) 15 pp.

Sperzel, et al., "Intraoperative Characterization of Interventricular Mechanical Dyssynchrony Using Electroanatomic Mapping System—A Feasibility Study," Journal of Interventional Cardiac Electrophysiology, published online Jun. 14, 2012, 35(2); (8 pages).

Study: "Integrated Diagnostics Driven Diuretic and Chronic Medication Management for Heart Failure." Sponsor: Medtronic Cardiac Rhythm and Heart Failure. https://clinicaltrials.gov/ct2/show/NCT02698241, last updated Apr. 2, 2018, 6 pp.

Sweeney, et al., "Analysis of Ventricular Activation Using Surface Electrocardiograma Predict Left Ventricular Reverse Volumetric Remolding During Cardiac Resynchronization Theraphy," Circulation, Journal of the American Heart Association, 2010:121:626-634, originally published online Jan. 25, 2010, (10 pages).

Tison et al., "Automated and Interpretable Patient ECG Profiles for Disease Detection, Tracking, and Discovery", Circulation: Cardiovascular Quality and Outcomes, Sep. 2019, 12 pp.

Trebbels et al., "Real-Time Cannula Navigation in Biological Tissue with High Temporal and Spatial Resolution Based on Impedance Spectroscopy", 32 Annual International Conference of the IEEE EMBS, Buenos Aires, Argentina, Aug. 31-Sep. 4, 2010, 4 pages.

Van Deursen et al., "Vectrocardiography as a Tool for Easy Optimization of Cardiac Resynchronization Therapy in Canine Left Bundle Branch Block Hearts," Circulation Arrhythmia and Electrophysiology, 2012:5:544-552, originally published online Apr. 24, 2012, (10 pages).

Virani et al. "Integrated Diagnostics for Heart Failure: The Triage-HF Study," Canadian Journal of Cardiology, Oct. 2016, vol. 32, Issue 10, Supplement 1, pp. S148-S149.

Yancy, MD et al. "2016 ACC/AHA/HFSA Focused Update on New Pharmacological Therapy for Heart Failure: An Update of the 2013 ACCF/AHA Guideline for the Management of Heart Failure," Journal of Cardiac Failure, vol. 22, No. 9, Sep. 2016, pp. 659-669.

Zheng et al., "An Automatic Diagnosis of Arrhythmias Using a Combination of CNN and LSTM Technology", Electronics 2020, Jan. 8, 2020, 15 pp.

Zhou et al., "Ensembling Neural Networks: Many Could Be Better Than All", Artificial Intelligence, 2002, vol. 137, No. 1-2, 23 pp.

Response to Written Opinion dated Aug. 19, 2022, from International Applicaiton No. PCT/US2022/031234, filed Oct. 19, 2022, 8 pp.

Breiman et al., "Bagging Predictors", vol. 24, Kluwer Academic Publishers, Aug. 2023, pp. 123-140, Retrieved from the Internet on Jan. 4, 2024 URL: https://link.springer.com/content/pdf/10.1007/BF00058655.pdf.

Chollet et al., "Deep Learning with Python", Simon & Schuster, Dec. 7, 2021, 373 pp., URL: http://silverio.net.br/heitor/disciplinas/eeica/papers/Livros/[Chollet]-Deep_Learning_with_Python.pdf.

Elliott et al., "Scientific Reproducibility, Human Error, and Public Policy", Bioscience, vol. 65, No. 1, Nov. 27, 2014, pp. 5-6, URL: https://academic.oup.com/bioscience/article/65/1/5/2754292.

Hannun et al., "Cardiologist-level arrhythmia detection and classification in ambulatory electrocardiograms using a deep neural network", Nature Medicine, vol. 25, No. 1, Jan. 2019, pp. 65-69, Retrieved from the Internet on Jan. 4, 2024 from URL: https://www.ncbi.nlm.nih.gov/pmc/articles/PMC6784839/.

He et al., "Deep Residual Learning for Image Recognition", Proceedings of the IEEE conference on computer vision and pattern recognition, Jun. 2016, pp. 770-778, Retrieved from the Internet on Jan. 4, 2024 from https://openaccess.thecvf.com/content_cvpr_2016/papers/He_Deep_Residual_Learning_CVPR_2016_paper.pdf.

Heaton et al., "Ian Goodfellow, Yoshua Bengio, and Aaron Courville: Deep learning", Springer, Oct. 29, 2017, pp. 305-307, URL: https://link.springer.com/article/10.1007/s10710-017-9314-z.

Hoffer et al., "Train longer, generalize better: Closing the generalization gap in large batch training of neural networks", May 24, 2017, 15 pp., Retrieved from the Internet on Jan. 4, 2024 from URL: http://arxiv.org/abs/1705.08741.

Huang et al., "Densely Connected Convolutional Networks", Proceedings of the IEEE conference on computer vision and pattern recognition, 2023, 9 pp., Retrieved from the Internet on Jan. 4, 2024 from URL: https://openaccess.thecvf.com/content_cvpr_2017/papers/Huang_Densely_Connected_Convolutional_CVPR_2017_paper.pdf ..

Jadhav et al., "Modular Neural Network Based Arrhythmia Classification System Using Signal Data", International Journal of Information Technology and Knowledge Management, vol. 4, No. 1, Jan. 2011, pp. 205-209, Retrieved from the Internet on Jan. 4,

(56)     References Cited

OTHER PUBLICATIONS 2024 from URL: https://www.csjournals.com/IJITKM/PDF%204-1/42.Shivajirao%20M.%20Jadhav1,%20Sanjay%20L.%20Nalbalwar2%20&%20Ashok%20A.%20Gh.pdf.

Keras et al., "Keras Applications", 4 pp., Retrieved from the Internet on Jan. 4, 2024 from URL: https://keras.io/api/applications/.

Kukacka et al., "Regularization for Deep Learning: A Taxonomy", arXiv:1710.1068v1, Oct. 29, 2017, 23 pp., URL: https://arxiv.org/abs/1710.10686.

Lin et al., "Network In Network", http://arxiv.org/abs/1312.4400v3, Mar. 4, 2014, 10 pp., URL: http://arxiv.org/abs/1312.4400.

Liu et al., "On the Variance of the Adaptive Learning Rate and Beyond", arXiv: 1908.03265v4, Oct. 26, 2021, 14 pp., URL: http://arxiv.org/abs/1908.03265.

Malach et al., "Proving the Lottery Ticket Hypothesis: Pruning is All You Need", International Conference on Machine Learning, PMLR, Nov. 21, 2020, pp. 6682-6691, URL: https://proceedings.mlr.press/v119/malach20a/malach20a.pdf.

Mattu et al., "Machine Bias", Angwin, May 23, 2016, 28 pp., URL: https://www.propublica.org/article/machine-bias-risk-assessments-in-criminal-sentencing.

Oord et al., "WaveNet: A Generative Model for Raw Audio", arXiv:1609.03499v2, Sep. 19, 2016, 15 pp., URL: https://arxiv.org/pdf/1609.03499.pdf?utm_source=Sailthru&utm_medium=email&utm_campaign=Uncubed%20Entry%20%2361%20-%20April%203%2C%202019&utm_term=entry.

Park et al., "ECG-Signal Multi-Classification Model Based on Squeeze-and-Excitation Residual Neural Networks", Applied Sciences, vol. 10, No. 18, Sep. 17, 2020, 8 pp., URL: https://doi.org/10.3390/app10186495.

Tensorflow, "Module: tf.keras.metrics", vol. 2, No. 14, 8 pp., Retrieved from the Internet on Jan. 4, 2024 URL: https://www.tensorflow.org/api_docs/python/tf/keras/metrics.

Wolpert et al., "No free lunch theorems for optimization", IEEE Transactions on Evolutionary Computation, vol. 1, No. 1, Apr. 1997, pp. 67-82, Retrieved from the Internet on Jan. 4, 2024 from URL: https://doi.org/10.1109/4235.585893.

Zhang et al., "Lookahead Optimizer: K steps forward, 1 step back", 33rd Conference on Neural Information Processing Systems, arXiv:1907.08610v2, Dec. 3, 2019, 12 pp., URL: http://arxiv.org/abs/1907.08610.

Zhang et al., "Understanding deep learning (still) requires rethinking generalization", Communications of the ACM, vol. 64, No. 3, Mar. 2021, 9 pp., Retrieved from the Internet on Jan. 4, 2024 from URL: http://arxiv.org/ abs/1611.03530.

Zhou et al., "Ensembling neural networks: Many could be better than all", ScienceDirect, No. 1-2, Elsevier, Nov. 16, 2001, pp. 239-263, URL: https://www.sciencedirect.com/science/article/pii/S000437020200190X.

Zhu et al., "Atrial Fibrillation Detection using Different Duration ECG Signals with SE-ResNet", IEEE 21st International Workshop on Multimedia Signal Processing (MMSP), Sep. 27, 2019, 5 pp., URL: https://doi.org/10.1109/MMSP.2019.8901729.

Kaur et al., "On the detection of Cardiac Arrhythmia with Principal Component Analysis", Wireless Personal Communication, vol. 97, Springer Business Media, LLC, Aug. 14, 2017, pp. 5495-5509.

Cantwell et al., "Rethinking multiscale cardiac electrophysiology with machine learning and predictive modelling", Computers in Biology and Medicine, vol. 104, Science Direct, Oct. 14, 2018, pp. 339-351.

Neuman et al., "Biopotential Electrodes", The Electrical Engineering Handbook, vol. 2, CRC Press LLC., 2000, 11 pp., (Applicant points out, in accordance with MPEP 609.04(a), that the year of publication, 2000, is sufficiently earlier than the effective U.S. filing date, so that the particular month of publication is not an issue. ).

Yancy, MD et al. "2013 ACCF/AHA Guideline for the Management of Heart Failure," Circulation, May 2013, 88 pp. e240-e327.

* cited by examiner

ADJUDICATION ALGORITHM BYPASS CONDITIONS

This application claims the benefit of U.S. Provisional Application Ser. No. 63/210,923, filed Jun. 15, 2021, the entire content of which is incorporated herein by reference.

FIELD

This disclosure generally relates to medical devices and, more particularly, analysis of signals sensed by medical devices.

BACKGROUND

Medical devices may be used to monitor physiological signals of a patient. For example, some medical devices are configured to sense cardiac electrogram (EGM) signals, e.g., electrocardiogram (ECG) signals, indicative of the electrical activity of the heart via electrodes. Some medical devices are configured to detect occurrences of cardiac arrhythmia, often referred to as episodes, based on the cardiac EGM and, in some cases, data from additional sensors. Example arrhythmia types include asystole, bradycardia, ventricular tachycardia, supraventricular tachycardia, wide complex tachycardia, atrial fibrillation, atrial flutter, ventricular fibrillation, atrioventricular block, premature ventricular contractions, and premature atrial contractions. The medical devices may store the cardiac EGM and other data collected during a time period including an episode as episode data. The medical device may also store episode data for a time period in response to user input, e.g., from the patient.

A computing system may obtain episode data from medical devices to allow a clinician or other user to review the episode. A clinician may diagnose a medical condition of the patient based on identified occurrences of cardiac arrhythmias within the episode. In some examples, a clinician or other reviewer may review episode data to annotate the episodes, including determining whether arrhythmias detected by the medical device actually occurred, to prioritize the episodes and generate reports for further review by the clinician that prescribed the medical device for a patient or is otherwise responsible for the care of the particular patient.

SUMMARY

In general, this disclosure describes techniques for bypassing an algorithm configured to classify episode data, including cardiac EGM data, as a true or false indication of a cardiac episode. In some examples, the processing circuitry receives the episode data and determines to bypass the algorithm based on satisfaction of one or more bypass conditions of a set of bypass conditions. Responsive to bypassing the algorithm, the processing circuitry stores the episode data as a true indication of the cardiac episode. Bypassing an algorithm in this way may provide one or more advantages. For example, satisfaction of the bypass conditions may indicate that the likelihood of a cardiac episode being true is such that adjudication by the algorithm may not be necessary and/or may incorrectly the identify the episode as false. As such, bypassing the algorithm in accordance with techniques of this disclosure may improve diagnosis of cardiac episodes and the quality of information provided from a medical system to caregivers.

In some examples, a method of monitoring a patient comprises: receiving, by processing circuitry of a medical device system, episode data for a cardiac episode; determining, by processing circuitry and based on satisfaction of one or more bypass conditions of a set of bypass conditions, to bypass an algorithm configured to determine a likelihood of the episode data being a false indication of the cardiac episode; and storing, by the processing circuitry and responsive to bypassing the algorithm, the episode data as a true indication of the cardiac episode.

In some examples, a medical device system comprises processing circuitry configured to: receive episode data for a cardiac episode; determine, based on satisfaction of one or more bypass conditions of a set of bypass conditions, whether to bypass an algorithm configured to determine a likelihood of the episode data being a false indication of the cardiac episode; and store, responsive to bypassing the algorithm, the episode data as a true indication of the cardiac episode.

In some examples, a computer-readable medium comprising instructions that, when executed, cause processing circuitry to: receive episode data; determine, based on satisfaction of one or more bypass conditions of a set of bypass conditions, whether to bypass an algorithm configured to determine a likelihood of the episode data being a false indication of a cardiac episode; and store, responsive to bypassing the algorithm, the episode data as a true indication of the cardiac episode.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF DRAWINGS

Like reference characters refer to like elements throughout the figures and description.

DETAILED DESCRIPTION

Figure 1:
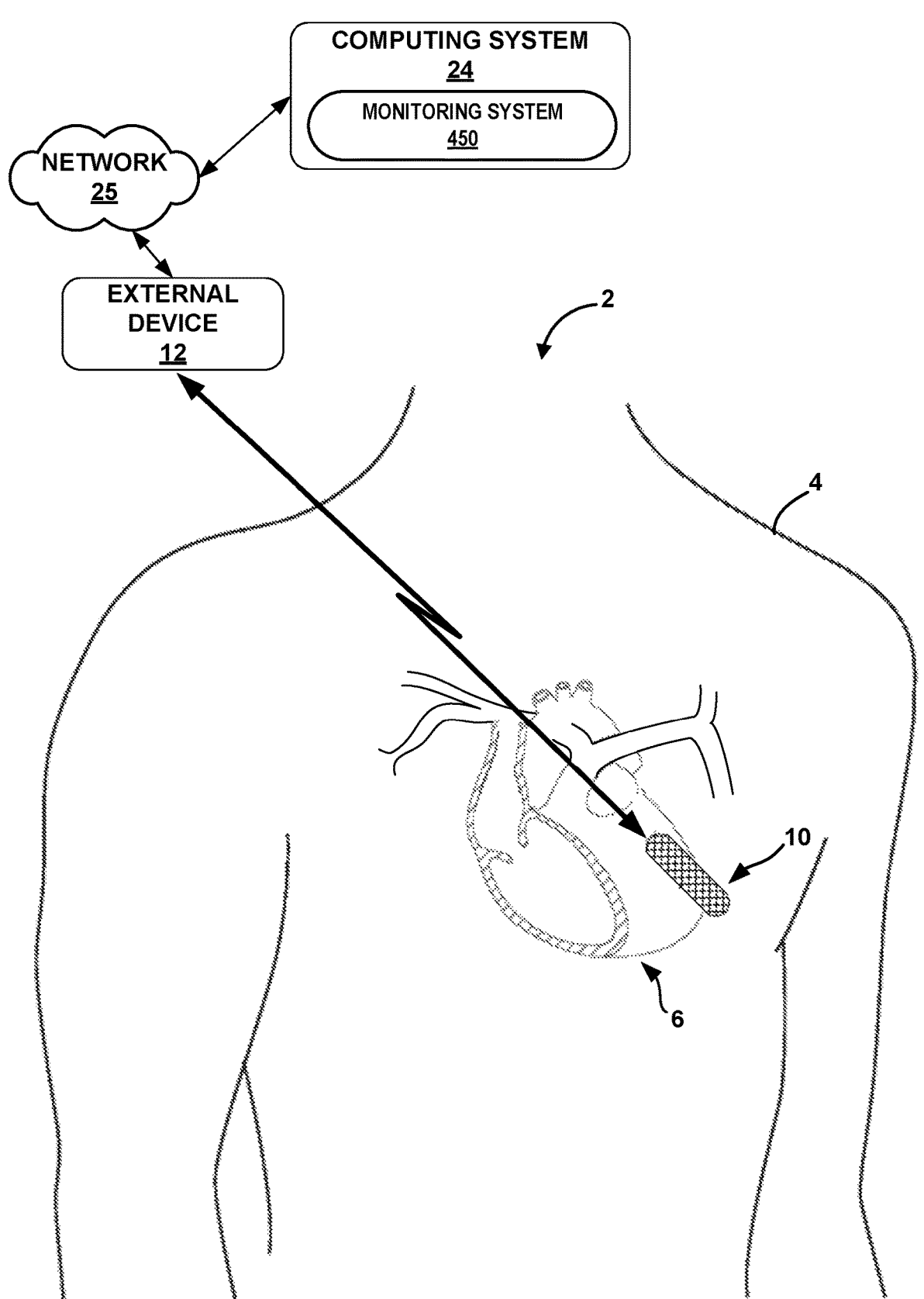
FIG. 1 is a conceptual drawing illustrating an example medical device system.

A variety of types of implantable and external medical devices detect arrhythmia episodes based on sensed cardiac EGMs and, in some cases, other physiological parameters. External devices that may be used to non-invasively sense and monitor cardiac EGMs include wearable devices with electrodes configured to contact the skin of the patient, such as patches, watches, rings, necklaces, or clothing. Such external devices may facilitate relatively longer-term monitoring of patients during normal daily activities, and may periodically transmit collected data, e.g., episode data for detected arrhythmia episodes, to a remote patient monitoring system (sometimes referred to herein as a "monitoring system"), such as the Medtronic Carelink™ Network.

Implantable medical devices (IMDs) can sense and monitor cardiac EGMs, and detect arrhythmia episodes. Example IMDs that monitor cardiac EGMs include pacemakers and implantable cardioverter-defibrillators, which may be coupled to intravascular or extravascular leads, as well as pacemakers with housings configured for implantation within the heart, which may be leadless. Some IMDs that do not provide therapy, e.g., implantable patient monitors, sense cardiac EGMs. One example of such an IMD is the Reveal LINQ™ Insertable Cardiac Monitor (ICM), available from Medtronic plc, which may be inserted subcutaneously. Such IMDs may facilitate relatively longer-term monitoring of patients during normal daily activities, and may periodically transmit collected data, e.g., episode data for detected arrhythmia episodes, to a remote patient monitoring system, such as the Medtronic Carelink™ Network.

By uploading episode data from medical devices, and distributing the episode data to various users, such network services may support centralized or clinic-based arrhythmia episode review. The episode data may include an indication of the one or more arrhythmias that the medical device detected during the episode. The episode data may also include data collected by the medical device during a time period including time before and after the instant the medical device determined the one or more arrhythmias to have occurred. The episode data may include the digitized cardiac EGM during that time period, heart rates or other parameters derived from the EGM during that time period, and any other physiological parameter data collected by the medical device during the time period.

Responsive to receiving the episode data, a remote patient monitoring system may be configured to review and annotate the episodes. In examples, the monitoring system may apply one or more atrial fibrillation (AF) adjudication algorithms, such as machine learning models, to the episode data to detect AF, time in AF, atrial tachycardia (AT), time in AT/AF, a pause (e.g., a prolonged R-R interval that represents the interruption in ventricular depolarization), and other types of arrythmias. In some cases, the adjudication algorithm of the monitoring system may classify episode data as either a true or false indication of a cardiac episode. These algorithms may help reduce the amount of time physicians spend reviewing episodes, in turn allowing them to focus on treating patients. Nonetheless, in certain scenarios, it may be preferable to bypass the algorithm and instead have a physician manually review the episode data.

This disclosure describes a medical device system that uses processing circuitry to bypass an adjudication algorithm of a monitoring system configured to classify episode data, including cardiac EGM data, as a true or false indication of a cardiac episode (e.g., AF episodes). The medical device system may include a medical device, such as one of the devices described above or any other type of implantable device, such as a subcutaneous cardiac monitoring device, a single chamber ICD, an extravascular ICD, a subcutaneous ICD, or any other type of device configured to classify detected cardiac episodes. The system may also include an external device, such as a cloud-based system that is external to the cardiac monitoring device, like Medtronic Carelink™ Network introduced above. The cloud-based system may include a monitoring system.

As cardiac monitoring devices are typically battery powered and, in the case of IMDs, need to have a sufficient enough battery life to justify implantation, the devices usually have limited processing capabilities in order to limit battery drain, which may limit the complexity of the algorithms that can be implemented inside the cardiac monitoring device. Thus, cardiac monitoring devices can be configured to transmit data collected for suspected cardiac episodes to the external system so the external system can use advanced signal processing techniques to post process stored and transmitted data for episodes prior to review by physicians. The transmission of data may be scheduled, occur in response to an event, such as abnormal heart activity, etc. For example, a cardiac monitoring device may transmit episode data on a daily basis to the external system. Additionally or alternatively, the cardiac monitoring system may send event-responsive transmissions. In such examples, the event may be something the cardiac monitoring device sensed (e.g., an episode that is considered severe because of type or severity in general) or a user request.

This disclosure describes advanced signal processing techniques that may be used by the external system to post process the episodes detected by the cardiac monitoring device. Although the techniques of this disclosure will be described as being performed by an external system, it should be understood that in other implementations the described techniques may be performed by the IMD itself or a device used to facilitate communication between the IMD and the external system, e.g., a smartphone, access point, or other edge device. As noted above, the medical device system may use processing circuitry to receive episode data. The processing circuitry of the medical device system may then determine whether to bypass an adjudication algorithm based on the satisfaction of one or more bypass conditions of a set of bypass conditions. Responsive to bypassing the adjudication algorithm, the processing circuitry may store the episode data as a true indication of a cardiac episode, such as an AF episode.

The set of bypass conditions may include various bypass conditions. One example bypass condition may be a time period condition. The medical device system may determine that the episode data satisfies the time period condition when the episode data received by the processing circuitry of the medical device system is a first transmission of episode data for the cardiac episode for a time period (e.g., a month). For example, if a transmission of episode data by a medical device to the medical device system is the first transmission of episode data during a time period of a particular month (e.g., May), then the medical device system may determine that the episode data satisfies the time period condition and bypass the adjudication algorithm of the monitoring system. Accordingly, the medical device system may store the episode data in memory (e.g., of the medical device system) for a physician to review.

In some examples, the time period may be based on a health condition of the patient. Example health conditions may include congestive heart failure, hypertension, age, diabetes, prior stroke, vascular disease, gender, etc. For example, if a patient has a health condition such as congestive heart failure, hypertension, diabetes, and/or a vascular disease, the time period may be relatively short (e.g., 7 to 14 days) to potentially increase the frequency at which the medical device system bypasses the adjudication algorithm. Additionally or alternatively, if a patient experiences a high frequency of episodes, the time period may be relatively short to potentially increase the frequency at which the medical device system bypasses the adjudication algorithm. In some examples, the medical device system may select a predetermined length of the time period based on the health condition of the patient. Additionally or alternatively, a physician may manually define the length of the time period.

In another example, if the transmission of episode data is a subsequent transmission of episode data (e.g., a second transmission of episode data) during the time period, then the medical device system may not bypass the adjudication algorithm, enabling the adjudication algorithm to determine the likelihood of the episode data being a true or false indication of a cardiac episode. Thus, the time period condition may ensure that the medical device system stores the first transmission of episode data for any given time period. This may be beneficial because the first transmission of episode data during a time period may be more relevant to a physician when treating a patient than subsequent transmissions of episode data during the same time period.

The set of bypass conditions may additionally or alternatively include an interval condition. The medical device system may determine that the episode data satisfies the interval condition when the episode data received by the processing circuitry of the medical device system is a first transmission of the episode data for the cardiac episode after an elapse of a time interval (e.g., 10 days) from a previous transmission of episode data for the cardiac episode. For example, if a transmission of episode data by a medical device to the medical device system is the first transmission of episode data after an elapse of a time interval of 10 days from a previous transmission of episode data for the cardiac episode, then the medical device system may determine that the episode data satisfies the interval condition and bypass the adjudication algorithm of the monitoring system. Accordingly, the medical device system may store the episode data in memory (e.g., of the medical device system) for a physician to review.

In another example, if the transmission of episode data is a transmission of episode data before the elapse of the time interval (e.g., a transmission of episode data with 2 days remaining before the elapse of the time interval), then the medical device system may not bypass the adjudication algorithm, enabling the adjudication algorithm to determine the likelihood of the episode data being a true or false indication of a cardiac episode. In this way, the interval condition may ensure that the medical device system stores a transmission of episode data that occurs at least a predetermined time interval after an immediately preceding transmission of episode data. This may be beneficial because the first transmission of episode data after an elapse of a time interval may be less likely to be a false indication of a cardiac episode, thus warranting review of the episode data by a physician.

As described below in greater detail, the set of bypass conditions may include additional bypass conditions, including, but not limited to, an implantation condition, a long-duration condition, a short duration condition, a user input condition, a frailty condition, a blood pressure condition, and/or the like. The set of bypass conditions may also include a very rapid rate with rate onset condition, a new onset condition, an increase in fluid retention or detection of a fall event condition, reduction in activity duration condition, etc. Further, in some examples, the processing circuitry of the medical device system may be configured to weigh each bypass condition of the set of bypass conditions to determine to bypass the adjudication algorithm. In such an example, the processing circuitry may assign a weight to each bypass condition of the set of bypass conditions, and, responsive to determining that the episode data satisfies one or more of the bypass conditions, calculate an aggregate weight of the one or more bypass conditions satisfied by the episode data. The processing circuitry may then determine to bypass the adjudication algorithm based on whether the aggregate weight satisfies the weight threshold. For example, if the aggregate weight exceeds a weight threshold value, then the processing circuitry may bypass the adjudication algorithm, storing the episode data in memory (e.g., of the medical device system) for a physician to review. In some examples, in addition to or alternative to calculating an aggregate weight of the one or more bypass conditions, the processing circuitry may determine satisfaction of the one or more bypass conditions using decision trees, random forests, fuzzy logic, etc.

Although primarily described with respect to remote patient monitoring systems, techniques of this disclosure may also apply to adjudication algorithms of medical devices, such as cardiac monitoring devices, that have the capability of adjudicating cardiac episodes. For example, a cardiac monitoring device may include application-specific processing circuitry configured to execute machine learning algorithms or other adjudication algorithms. Thus, a medical device, e.g., an insertable cardiac monitor or other implantable medical device, may be configured to perform one or more techniques of the present disclosure alone. In such an example, however, it may be unnecessary to transmit the episode data across a network (e.g., because collecting the episode data and adjudicating the episode data may be performed by the same medical device).

FIG. 1 is a conceptual drawing illustrating an example of a medical device system 2 configured to bypass an adjudication algorithm in accordance with the techniques of the disclosure. The example techniques may be used with an IMD 10, which may be in wireless communication with an external device 12. In some examples, IMD 10 is implanted outside of a thoracic cavity of patient 4 (e.g., subcutaneously in the pectoral location illustrated in FIG. 1). IMD 10 may be positioned near the sternum near or just below the level of the heart 6 of patient 4, e.g., at least partially within the cardiac silhouette. IMD 10 includes a plurality of electrodes (not shown in FIG. 1), and is configured to sense a cardiac EGM via the plurality of electrodes. In some examples, IMD 10 takes the form of the LINQ™ ICM. Although described primarily in the context of examples in which the medical device that collects episode data takes the form of an ICM, the techniques of this disclosure may be implemented in systems including any one or more implantable or external medical devices, including monitors, pacemakers, or defibrillators.

External device 12 is a computing device configured for wireless communication with IMD 10. External device 12 may be, as examples, a mobile telephone or other computing device of patient 4 or another user, or a computing device detected to communication with IMD 10. External device 12 may be configured to communicate with computing system 24 via network 25. In some examples, external device 12 may provide a user interface and allow a user to interact with IMD 10. Computing system 24 may comprise computing devices configured to allow a user to interact with IMD 10, or data collected from IMD, via network 25.

External device 12 may be used to retrieve data from IMD 10 and may transmit the data to computing system 24 via network 25. The retrieved data may include values of physiological parameters measured by IMD 10, indications of episodes of arrhythmia or other maladies detected by IMD 10, episode data collected for episodes, and other physiological signals recorded by IMD 10. The episode data may include EGM segments recorded by IMD 10, e.g., due to IMD 10 determining that an episode of arrhythmia or another malady occurred during the segment, or in response to a request to record the segment from patient 4 or another user.

In some examples, computing system 24 includes one or more handheld computing devices, computer workstations, servers or other networked computing devices. In some examples, computing system 24 may include one or more devices, including processing circuitry and storage devices, that implement a monitoring system 450. Computing system 24, network 25, and monitoring system 450 may be implemented by the Medtronic Carelink™ Network or other patient monitoring system, in some examples.

Network 25 may include one or more computing devices (not shown), such as one or more non-edge switches, routers, hubs, gateways, security devices such as firewalls, intrusion detection, and/or intrusion prevention devices, servers, computer terminals, laptops, printers, databases, wireless mobile devices such as cellular phones or personal digital assistants, wireless access points, bridges, cable modems, application accelerators, or other network devices. Network 25 may include one or more networks administered by service providers, and may thus form part of a large-scale public network infrastructure, e.g., the Internet. Network 25 may provide computing devices, such as computing system 24 and IMD 10, access to the Internet, and may provide a communication framework that allows the computing devices to communicate with one another. In some examples, network 25 may be a private network that provides a communication framework that allows computing system 24, IMD 10, and/or external device 12 to communicate with one another but isolates one or more of computing system 24, IMD 10, or external device 12 from devices external to network 25 for security purposes. In some examples, the communications between computing system 24, IMD 10, and external device 12 are encrypted.

Monitoring system 450, e.g., implemented by processing circuitry of computing system 24, may implement the techniques of this disclosure including applying machine learning models or other models or algorithms to episode data to detect cardiac arrhythmias. Monitoring system 450 may receive episode data for episodes from medical devices, including IMD 10, which may store the episode data in response to their detection of an arrhythmia and/or user input. Based on the application of one or more arrhythmia classification algorithms, monitoring system 450 may determine the likelihood that one or more arrhythmias of one or more types occurred during the episode including, in some examples, the arrhythmia identified by the medical device that stored the episode data. Monitoring system 450 may, for example, receive episode data, e.g., ECG data, for an episode of a patient from IMD 10. Monitoring system 450 may then apply one or more algorithms, such as a machine learning model, to classify the episode data as a true or false indication of a cardiac episode.

Processing circuitry of medical device system 2 (e.g., of IMD 10, external device 12, computing system 24, and/or of one or more other computing devices) may be configured to perform the example techniques of this disclosure for bypassing an algorithm configured to classify episode data, including cardiac EGM data, as a true or false indication of a cardiac episode. Responsive to processing circuitry of medical device system 2 receiving episode data, the processing circuitry may determine whether to bypass the adjudication algorithm based on the satisfaction of one or more bypass conditions of a set of bypass conditions, discussed in greater detail with respect to FIG. 4. Responsive to bypassing the adjudication algorithm, the processing circuitry may store the episode data as a true indication of a cardiac episode, such as an AF episode.

Figure 2:
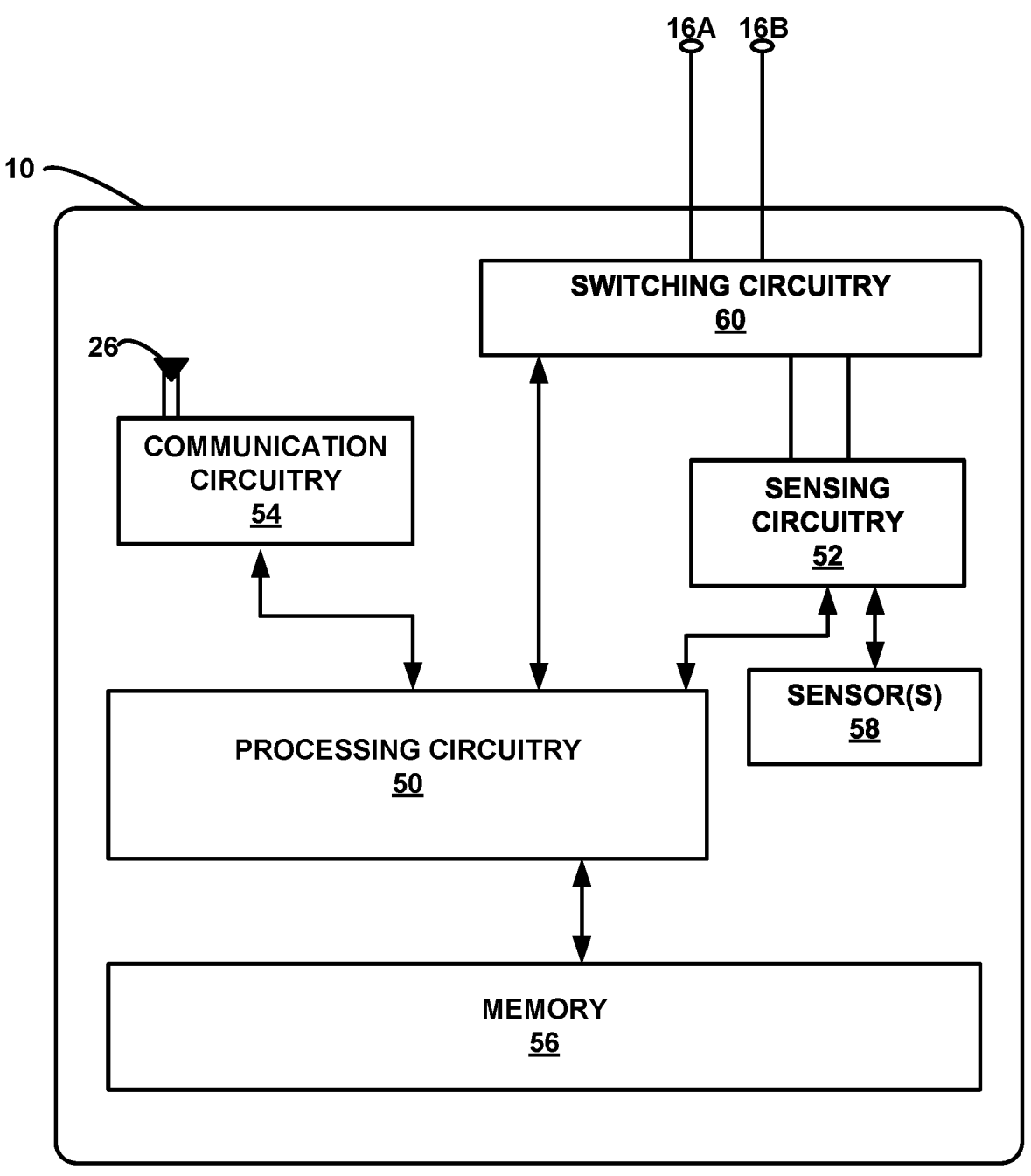
FIG. 2 is a block diagram illustrating an example configuration of the implantable medical device (IMD) of FIG. 1.

FIG. 2 is a block diagram illustrating an example configuration of IMD 10 of FIG. 1. As shown in FIG. 2, IMD 10 includes processing circuitry 50 sensing circuitry 52, communication circuitry 54, memory 56, sensors 58, switching circuitry 60, and electrodes 16A, 16B (hereinafter "electrodes 16"), one or more of which may be disposed on a housing of IMD 10. In some examples, memory 56 includes computer-readable instructions that, when executed by processing circuitry 50, cause IMD 10 and processing circuitry 50 to perform various functions attributed herein to IMD 10 and processing circuitry 50. Memory 56 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

Sensing circuitry 52 may be selectively coupled to electrodes 16A, 16B via switching circuitry 60 as controlled by processing circuitry 50. Sensing circuitry 52 may monitor signals from electrodes 16A, 16B in order to monitor electrical activity of a heart of patient 4 of FIG. 1 and produce cardiac EGM data for patient 4. In some examples, processing circuitry 50 may identify features of the sensed cardiac EGM to detect an episode of cardiac arrhythmia of patient 4. Processing circuitry 50 may store the digitized cardiac EGM and features of the EGM used to detect the arrhythmia episode in memory 56 as episode data for the detected arrhythmia episode. In some examples, processing circuitry 50 stores one or more segments of the cardiac EGM data, features derived from the cardiac EGM data, and other episode data in response to instructions from external device 12 (e.g., when patient 4 experiences one or more symptoms of arrhythmia and inputs a command to external device 12 instructing IMD 10 to upload the data for analysis by a monitoring center or clinician).

In some examples, processing circuitry 50 transmits, via communication circuitry 54, the episode data for patient 4 to an external device, such as external device 12 of FIG. 1. For example, IMD 10 sends digitized cardiac EGM and other episode data to network 25 for processing by monitoring system 450 of FIG. 1.

Sensing circuitry 52 and/or processing circuitry 50 may be configured to detect cardiac depolarizations (e.g., P-waves of atrial depolarizations or R-waves of ventricular depolarizations) when the cardiac EGM amplitude crosses a sensing threshold. For cardiac depolarization detection, sensing circuitry 52 may include a rectifier, filter, amplifier, comparator, and/or analog-to-digital converter, in some examples. In some examples, sensing circuitry 52 may output an indication to processing circuitry 50 in response to sensing of a cardiac depolarization. In this manner, processing circuitry 50 may receive detected cardiac depolarization indicators corresponding to the occurrence of detected R-waves and P-waves in the respective chambers of heart. Processing circuitry 50 may use the indications of detected R-waves and P-waves for determining features of the cardiac EGM including inter-depolarization intervals, heart rate, and detecting arrhythmias, such as tachyarrhythmias and asystole. Sensing circuitry 52 may also provide one or more digitized cardiac EGM signals to processing circuitry 50 for analysis, e.g., for use in cardiac rhythm discrimination and/or to identify and delineate features of the cardiac EGM, such as QRS amplitudes and/or width, or other morphological features.

In some examples, IMD 10 includes one or more sensors 58, such as one or more accelerometers, microphones, optical sensors, and/or pressure sensors. In some examples, sensing circuitry 52 may include one or more filters and amplifiers for filtering and amplifying signals received from one or more of electrodes 16A, 16B and/or other sensors 58. In some examples, sensing circuitry 52 and/or processing circuitry 50 may include a rectifier, filter and/or amplifier, a sense amplifier, comparator, and/or analog-to-digital converter. Processing circuitry 50 may determine values of physiological parameters of patient 4 based on signals from sensors 58, which may be used to identify arrhythmia episodes and stored as episode data in memory 56.

Communication circuitry 54 may include any suitable hardware, firmware, software or any combination thereof for communicating with another device, such as external device 12. Communication circuitry 54 may be configured to communicate using any of a variety of wireless communication schemes, such as Bluetooth® or Bluetooth Low Energy®. Under the control of processing circuitry 50, communication circuitry 54 may receive downlink telemetry from, as well as send uplink telemetry to, external device 12 or another device with the aid of an internal or external antenna, e.g., antenna 26. In some examples, processing circuitry 50 may communicate with a networked computing device via an external device (e.g., external device 12) and a computer network, such as the Medtronic CareLink® Network developed by Medtronic, plc, of Dublin, Ireland.

Although described herein in the context of example IMD 10, the techniques for cardiac arrhythmia detection disclosed herein may be used with other types of devices. For example, the techniques may be implemented with an extra-cardiac defibrillator coupled to electrodes outside of the cardiovascular system, a transcatheter pacemaker configured for implantation within the heart, such as the Micra™ transcatheter pacing system commercially available from Medtronic PLC of Dublin Ireland, an insertable cardiac monitor, such as the Reveal LINQ™ ICM, also commercially available from Medtronic PLC, a neurostimulator, a drug delivery device, a medical device external to patient 4, a wearable device such as a wearable cardioverter defibrillator, a fitness tracker, or other wearable device, a mobile device, such as a mobile phone, a "smart" phone, a laptop, a tablet computer, a personal digital assistant (PDA), or "smart" apparel such as "smart" glasses, a "smart" patch, or a "smart" watch.

Figure 3:
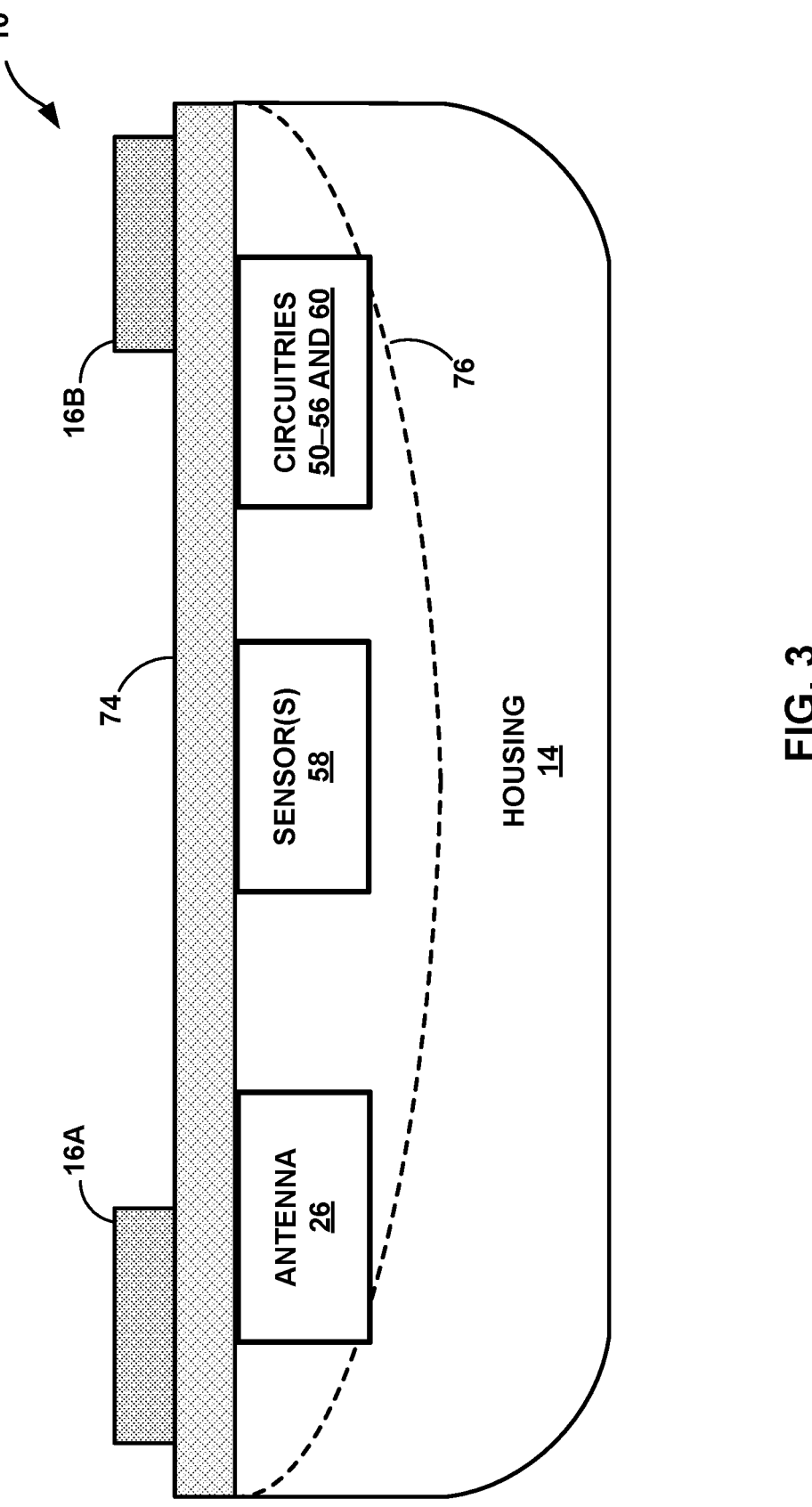
FIG. 3 is a conceptual side-view diagram illustrating an example configuration of the IMD of FIGS. 1 and 2.

FIG. 3 is a conceptual side-view diagram illustrating an example configuration of IMD 10. In the example shown in FIG. 3, IMD 10 may include a leadless, subcutaneously-implantable monitoring device having a housing 14 and an insulative cover 74. Electrode 16A and electrode 16B may be formed or placed on an outer surface of cover 74. Circuitries 50-56 and 60, described above with respect to FIG. 2, may be formed or placed on an inner surface of cover 74, or within housing 14. In the illustrated example, antenna 26 is formed or placed on the inner surface of cover 74, but may be formed or placed on the outer surface in some examples. Sensors 58 may also be formed or placed on the inner or outer surface of cover 74 in some examples. In some examples, insulative cover 74 may be positioned over an open housing 14 such that housing 14 and cover 74 enclose antenna 26, sensors 58, and circuitries 50-56 and 60, and protect the antenna and circuitries from fluids such as body fluids.

One or more of antenna 26, sensors 58, or circuitries 50-56 may be formed on insulative cover 74, such as by using flip-chip technology. Insulative cover 74 may be flipped onto a housing 14. When flipped and placed onto housing 14, the components of IMD 10 formed on the inner side of insulative cover 74 may be positioned in a gap 76 defined by housing 14. Electrodes 16 may be electrically connected to switching circuitry 60 through one or more vias (not shown) formed through insulative cover 74. Insulative cover 74 may be formed of sapphire (i.e., corundum), glass, parylene, and/or any other suitable insulating material. Housing 14 may be formed from titanium or any other suitable material (e.g., a biocompatible material). Electrodes 16 may be formed from any of stainless steel, titanium, platinum, iridium, or alloys thereof. In addition, electrodes 16 may be coated with a material such as titanium nitride or fractal titanium nitride, although other suitable materials and coatings for such electrodes may be used.

Figure 4:
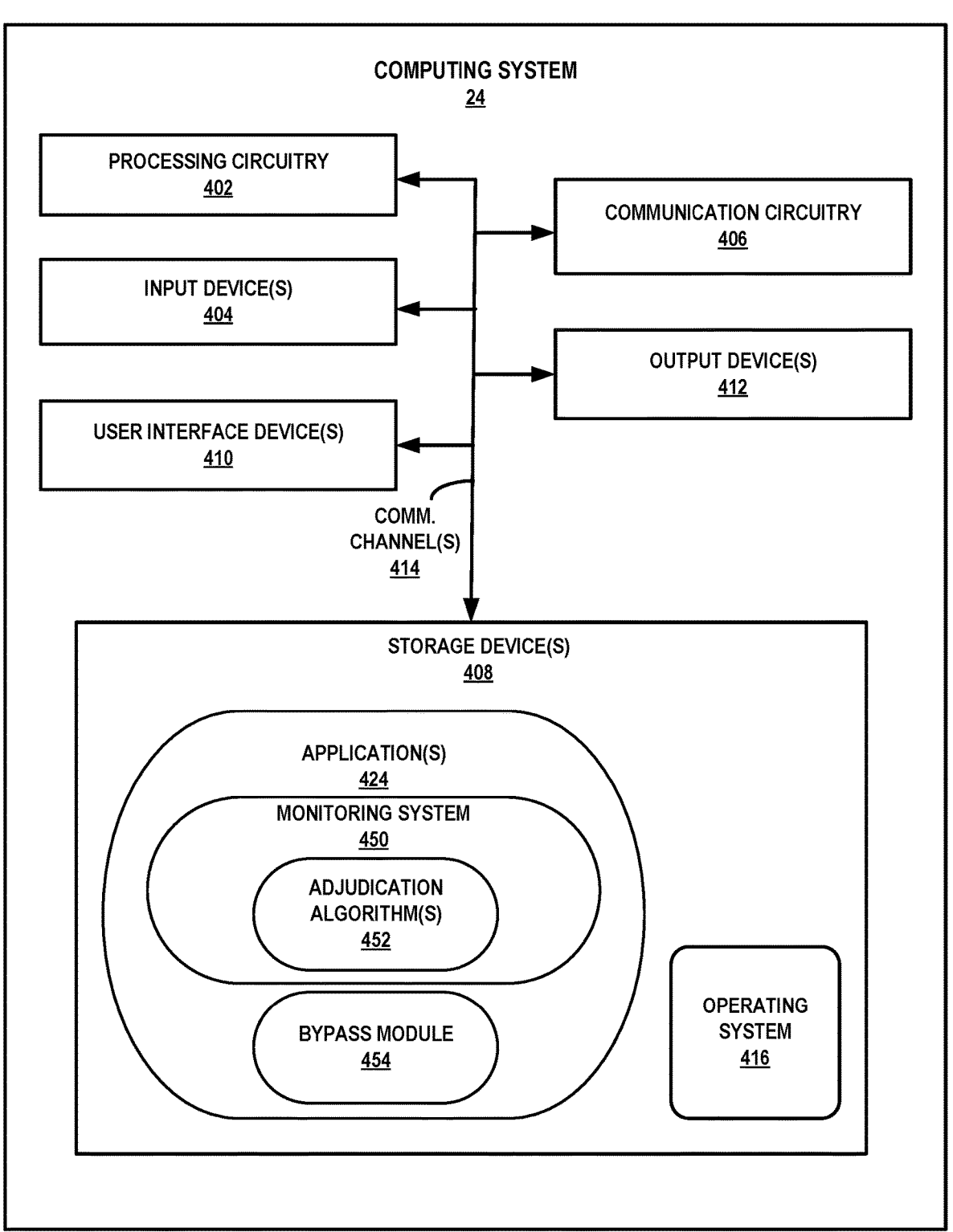
FIG. 4 is a functional block diagram illustrating an example configuration of the computing system of FIG. 1.

FIG. 4 is a block diagram illustrating an example configuration of computing system 24. In the illustrated example, computing system 24 includes processing circuitry 402 for executing applications 424 that include monitoring system 450 or any other applications described herein. Computing system 24 may be any component or system that includes processing circuitry or other suitable computing environment for executing software instructions and, for example, need not necessarily include one or more elements shown in FIG. 4 (e.g., input devices 404, communication circuitry 406, user interface devices 410, or output devices 412; and in some examples components such as storage device(s) 408 may not be co-located or in the same chassis as other components). In some examples, computing system 24 may be a cloud computing system distributed across a plurality of devices.

In the example of FIG. 4, computing system 24 includes processing circuitry 402, one or more input devices 404, communication circuitry 406, one or more storage devices 408, user interface (UI) device(s) 410, and one or more output devices 412. Computing system 24, in some examples, further includes one or more application(s) 424 such as monitoring system 450, and operating system 416 that are executable by computing system 24. Each of components 402, 404, 406, 408, 410, and 412 may be coupled (physically, communicatively, and/or operatively) for inter-component communications. In some examples, communication channels 414 may include a system bus, a network connection, an inter-process communication data structure, or any other method for communicating data. As one example, components 402, 404, 406, 408, 410, and 412 may be coupled by one or more communication channels 414.

Processing circuitry 402, in one example, is configured to implement functionality and/or process instructions for execution within computing system 24. For example, processing circuitry 402 may be capable of processing instructions stored in storage device 408. Examples of processing circuitry 402 may include any one or more of a microprocessor, a controller, a digital signal processor (DSP), an application specific integrated circuit (ASIC), a field-programmable gate array (FPGA), or equivalent discrete or integrated logic circuitry.

One or more storage devices 408 may be configured to store information within computing device during operation. Storage device 408, in some examples, is described as a computer-readable storage medium. In some examples, storage device 408 is a temporary memory, meaning that a primary purpose of storage device 408 is not long-term storage. Storage device 408, in some examples, is described as a volatile memory, meaning that storage device 408 does not maintain stored contents when the computer is turned off. Examples of volatile memories include RAM, dynamic random access memories (DRAM), static random access memories (SRAM), and other forms of volatile memories known in the art. In some examples, storage device 408 is used to store program instructions for execution by processing circuitry 402. Storage device 408, in one example, is used by software or applications 424 running on computing system 24 to temporarily store information during program execution.

Storage devices 408, in some examples, also include one or more computer-readable storage media. Storage devices 408 may be configured to store larger amounts of information than volatile memory. Storage devices 408 may further be configured for long-term storage of information. In some examples, storage devices 408 include non-volatile storage elements. Examples of such non-volatile storage elements include magnetic hard discs, optical discs, floppy discs, flash memories, or forms of electrically programmable memories (EPROM) or electrically erasable and programmable memories (EEPROM).

Computing system 24, in some examples, also includes communication circuitry 406 to communicate with other devices and systems, such as IMD 10 and external device 12 of FIG. 1. Communication circuitry 406 may include a network interface card, such as an Ethernet card, an optical transceiver, a radio frequency transceiver, or any other type of device that can send and receive information. Other examples of such network interfaces may include 3G, 4G, 5G, and WiFi® radios.

Computing system 24, in one example, also includes one or more user interface devices 410. User interface devices 410, in some examples, are configured to receive input from a user through tactile, audio, or video feedback. Examples of user interface devices(s) 410 include a presence-sensitive display, a mouse, a keyboard, a voice responsive system, video camera, microphone or any other type of device for detecting a command from a user. In some examples, a presence-sensitive display includes a touch-sensitive screen.

One or more output devices 412 may also be included in computing system 24. Output devices 412, in some examples, are configured to provide output to a user using tactile, audio, or video stimuli. Output devices 412, in one example, include a presence-sensitive display, a sound card, a video graphics adapter card, or any other type of device for converting a signal into an appropriate form understandable to humans or machines. Additional examples of output devices 412 include a speaker, a cathode ray tube (CRT) monitor, a liquid crystal display (LCD), or any other type of device that can generate intelligible output to a user.

Computing system 24 may include operating system 416. Operating system 416, in some examples, controls the operation of components of computing system 24. For example, operating system 416, in one example, facilitates the communication of one or more applications 424 and monitoring system 450 with processing circuitry 402, communication circuitry 406, storage device 408, input device 404, user interface devices 410, and output device 412.

Applications 424 may also include program instructions and/or data that are executable by computing device. Example application(s) 424 executable by computing device 400 may include monitoring system 450. Other additional applications not shown may alternatively or additionally be included to provide other functionality described herein and are not depicted for the sake of simplicity.

Computing system 24 may receive episode data for episodes stored by medical devices, such as IMD 10, via communication circuitry 406. Storage device 408 may store the episode data for the episodes in storage device 408. The episode data may have been collected by the medical devices in response to the medical devices detecting arrhythmias and/or user input directing the storage of episode data.

Monitoring system 450, as implemented by processing circuitry 402, may review and annotate the episodes, and generate reports or other presentations of the episodes subsequent to the annotation for review by a clinician or other reviewer. Monitoring system 450 may utilize input devices 404, output devices 412, and/or communication circuitry 406 to display episode data, arrhythmia type classifications, and any other information described herein to users, and to receive any annotations or other input regarding the episode data from the users.

In the example illustrated by FIG. 4, monitoring system 450 may apply one or more adjudication algorithms 452 to episode data. Adjudication algorithm 452 may include, as examples, neural networks, such as deep neural networks, which may include convolutional neural networks, multi-layer perceptrons, and/or echo state networks, as examples. In examples, adjudication algorithm 452 represents one or more arrhythmia classification machine learning models. Adjudication algorithm 452 may be configured to output, for each of a plurality of arrhythmia type classifications, values indicative of the likelihood that an arrhythmia of the type occurred at any point during the episode. Monitoring system 450 may apply configurable thresholds (e.g., 50%, 75%, 90%, 95%, 99%) to the likelihood values to identify the episode as including one or more arrhythmia types, e.g., based on the likelihood for that classification meeting or exceeding the threshold. Although FIG. 4 illustrates an example in which monitoring system 450 applies one or more adjudication algorithms 452 as part of its algorithm to classify arrhythmias, in some examples the algorithm includes other artificial intelligence, or other models or algorithms that do not necessarily require machine learning, such as linear regression, trend analysis, decision trees, rules, or thresholds.

In accordance with the techniques of the disclosure, processing circuitry 402 is configured to execute computer-readable instructions stored within storage devices 408 that cause processing circuitry 402 to bypass adjudication algorithm 452 configured to classify episode data as a true or false indication of a cardiac episode. As noted above, processing circuitry 402 may, in response to receiving episode data, determine whether to bypass adjudication algorithm 452 based on the satisfaction of one or more bypass conditions of a set of bypass conditions. Responsive to bypassing adjudication algorithm 452, processing circuitry 402 may store the episode data as a true indication of a cardiac episode, such as an AF episode.

The set of bypass conditions may include various bypass conditions. One example bypass condition may be a time period condition. Processing circuitry 402 may determine that the episode data satisfies the time period condition when the episode data received by processing circuitry 402 is a first transmission of the episode data for the cardia episode for a time period (e.g., a month). In some examples, the time period may be based on a health condition of the patient. Example health conditions may include congestive heart failure, hypertension, age, diabetes, prior stroke, vascular disease, gender, etc. For example, if a patient has a health condition such as congestive heart failure, hypertension, diabetes, and/or a vascular disease, the time period may be relatively short (e.g., 7 to 14 days) to potentially increase the frequency at which the medical device system bypasses adjudication algorithm 452. In some examples, the medical device system may select a predetermined length of the time period based on the health condition of the patient. Additionally or alternatively, a physician may manually define the length of the time period.

In an example, if a transmission of episode data by IMD 10 to medical device system 2 is the first transmission of episode data during a time period of a particular month (e.g., May), then processing circuitry 402 may determine that the episode data satisfies the time period condition and bypass adjudication algorithm 452. Accordingly, processing circuitry 402 may store the episode data in memory (e.g., storage devices 408) for a physician to review.

In another example, if the transmission of episode data is a subsequent transmission of episode data (e.g., a second transmission of episode data) during the time period, then processing circuitry 402 may not bypass adjudication algorithm 452, enabling adjudication algorithm 452 to determine the likelihood of the episode data being a true or false indication of a cardiac episode. Thus, the time period condition may ensure that medical device system 2 stores the first transmission of episode data for any given time period. This may be beneficial because the first transmission of episode data during a time period may be more relevant to a physician when treating a patient than subsequent transmissions of episode data during the same time period.

The set of bypass conditions may additionally or alternatively include an interval condition. Processing circuitry 402 may determine that the episode data satisfies the interval condition when the episode data received by processing circuitry 402 is a first transmission of the episode data for the cardiac episode after an elapse of a time interval (e.g., 10 days) from a previous transmission of episode data for the cardiac episode. For example, if a transmission of episode data by IMD 10 to medical device system 2 is the first transmission of episode data after an elapse of a time interval of 10 days from a previous transmission of episode data for the cardiac episode, then processing circuitry 402 may determine that the episode data satisfies the interval condition and bypass adjudication algorithm 452. Accordingly, medical device system 2 may store the episode data in memory for a physician to review.

In another example, if the transmission of episode data is a transmission of episode data before the elapse of the time interval (e.g., a transmission of episode data with 2 days remaining before the elapse of the time interval), then medical device system 2 may not bypass adjudication algorithm 452, enabling adjudication algorithm 452 to determine the likelihood of the episode data being a true or false indication of a cardiac episode. In this way, the interval condition may ensure that medical device system 2 stores a transmission of episode data that occurs at least a predetermined time interval after an immediately preceding transmission of episode data. This may be beneficial because the first transmission of episode data after an elapse of a time interval may be less likely to be a false indication of a cardiac episode, thus warranting review of the episode data by a physician.

The set of bypass conditions may additionally or alternatively include an implantation condition. Processing circuitry 402 may determine that the episode data satisfies the implantation condition when the episode data received by processing circuitry 402 is one of a first N transmissions of the episode data for the cardiac episode after implantation of IMD 10 of medical device system 2. For example, if N is 10 and a transmission of episode data by IMD 10 to medical device system 2 is the fifth transmission of episode data after implantation of IMD 10, then processing circuitry 402 may determine that the episode data satisfies the implantation condition and bypass adjudication algorithm 452. Accordingly, medical device system 2 may store the episode data in memory for a physician to review.

In another example, if the transmission of episode data is the eleventh transmission of episode data after implantation of IMD 10, then medical device system 2 may not bypass adjudication algorithm 452, enabling adjudication algorithm 452 to determine the likelihood of the episode data being a true or false indication of a cardiac episode. In this way, the implantation condition may ensure that medical device system 2 stores the first N transmissions of episode data after implantation of IMD 10. This may be beneficial because the first N transmissions of episode data after implantation of IMD 10 may be less likely to be a false indication of a cardiac episode, thus warranting review of the episode data by a physician. It should be understood that N may be any number of transmissions, such as 5, 8, 12, 20, etc.

The set of bypass conditions may additionally or alternatively include a long duration condition. Processing circuitry 402 may determine that the episode data satisfies the long duration condition when a duration of the episode data received by processing circuitry 402 exceeds a long duration threshold value. For example, if the long duration threshold value is 30 minutes and the duration of the episode data received by processing circuitry 402 is 31 minutes, then processing circuitry 402 may determine that the episode data satisfies the long duration condition and bypass adjudication algorithm 452. Accordingly, medical device system 2 may store the episode data in memory for a physician to review.

In another example, if the duration of the episode data is 15 minutes, then medical device system 2 may not bypass adjudication algorithm 452, enabling adjudication algorithm 452 to determine the likelihood of the episode data being a true or false indication of a cardiac episode. In this way, the long duration condition may ensure that medical device system 2 stores episode data with a duration equal to or greater than a long duration threshold value. This may be beneficial because episode data with a duration equal to or greater than a long duration threshold value may be less likely to be a false indication of a cardiac episode, thus warranting review of the episode data by a physician.

The set of bypass conditions may additionally or alternatively include a short duration condition. Processing circuitry 402 may determine that the episode data satisfies the short duration condition when a duration of the episode data received by processing circuitry 402 is less than a short duration threshold value. For example, if the short duration threshold value is 2 seconds and the duration of the episode data received by processing circuitry 402 is 1 second, then processing circuitry 402 may determine that the episode data satisfies the short duration condition and bypass adjudication algorithm 452. Accordingly, medical device system 2 may store the episode data in memory for a physician to review.

In another example, if the duration of the episode data is 3 seconds, then medical device system 2 may not bypass adjudication algorithm 452, enabling adjudication algorithm 452 to determine the likelihood of the episode data being a true or false indication of a cardiac episode. In this way, the short duration condition may ensure that medical device system 2 stores episode data with a duration less than a short duration threshold value. This may be beneficial because a physician may have specifically programmed the asystole detection interval to be relatively short (e.g., 2 seconds or less) because the physician considers episode data having such an interval to be clinically significant events, thus warranting review of the episode data by the physician.

The set of bypass conditions may additionally or alternatively include a user input condition. Processing circuitry 402 may determine that the episode data satisfies the user input condition when the user provides a user input (e.g., actuation of a user interface) that causes processing circuitry 402 to bypass the algorithm for a bypass period. For example, if the user presses a button on external device 12 associated with bypassing adjudication algorithm 452, then processing circuitry 402 may determine that the user input condition is satisfied and bypass adjudication algorithm 452 for a bypass period (e.g., a predetermined range of time beginning before the user input and ending after the user input). Accordingly, medical device system 2 may store the episode data in memory for a physician to review. This may be beneficial because a user may press the button whenever the user experiences symptoms of a potential cardiac episode. Accordingly, episode data occurring within a range of time of the user input (e.g., a few minutes before the user input until a few minutes after the user input) is less likely to be a false indication of a cardiac episode, thus warranting review of the episode data by the physician.

The set of bypass conditions may additionally or alternatively include a frailty condition. Processing circuitry 402 may determine that the episode data satisfies the frailty condition when a transmission of episode data for the cardiac episode occurs within a time window during which the patient at least one of falls or exhibits body instability (e.g., abnormal stride patterns, imbalance after standing, increased time to transition from standing to sitting, etc.). An accelerometer, gyroscope, and/or the like, e.g., included among sensor(s) 58 of IMD 10 or in external device 12, may be used to detect whether the patient has fallen or exhibits body instability. For example, an accelerometer may be used to monitor the variability of stride duration to detect an abnormal stride pattern, body stability (e.g., balance) after standing, amount of time to transition from sitting to standing and vice versa, etc.

As one example of processing circuitry 402 bypassing adjudication algorithm 452, if the beginning of a time window is 30 minutes before the occurrence of a fall or body instability, the end of the time window is 30 minutes after the occurrence of a fall or body instability, and the transmission of episode data for the cardiac episode occurs 15 minutes after the occurrence of a fall (e.g., detected by an accelerometer of IMD 10), then processing circuitry 402 may determine that the episode data satisfies the frailty condition and bypass adjudication algorithm 452. Accordingly, medical device system 2 may store the episode data in memory for a physician to review.

In another example, if the beginning of a time window is 30 minutes before the occurrence of a fall or body instability, the end of the time window is 30 minutes after the occurrence of a fall or body instability, and the transmission of episode data for the cardiac episode occurs 40 minutes before the occurrence of a fall (e.g., detected by an accelerometer of IMD 10), then processing circuitry 402 may not bypass adjudication algorithm 452, enabling adjudication algorithm 452 to determine the likelihood of the episode data being a true or false indication of a cardiac episode. In this way, the frailty condition may ensure that medical device system 2 stores episode data that occurs within a time window during which the patient at least one of falls or exhibits body instability. This may be beneficial because the transmission of episode data within such a time window may be less likely to be a false indication of a cardiac episode, thus warranting review of the episode data by a physician.

The set of bypass conditions may additionally or alternatively include a blood pressure condition. Processing circuitry 402 may determine that the episode data satisfies the blood pressure condition when a transmission of episode data for the cardiac episode occurs within a time window during which a change in blood pressure of the patient exceeds a blood pressure threshold value. For example, an optical sensor may be used to detect whether a change in blood pressure (e.g., systolic, diastolic, etc.) of the patient exceeds a blood pressure threshold value. Additionally or alternatively, processing circuitry 402 may bypass adjudication algorithm 452 based on a Pulse Transit Time (PTT), which may be correlated with blood pressure, instead of blood pressure because blood pressure may be difficult to continuously monitor (e.g., using IMD 10).

As one example of processing circuitry 402 bypassing adjudication algorithm based on blood pressure, if the blood pressure threshold value is 20 millimeters of mercury (mmHg), the change in the systolic pressure is 40 mmHg, the beginning of a time window is 30 minutes before the occurrence of this change in blood pressure, the end of the time window is 30 minutes after the occurrence of change in blood pressure, and the transmission of episode data for the cardiac episode occurs 20 minutes after the occurrence of the change in blood pressure, then processing circuitry 402 may determine that the episode data satisfies the blood pressure condition and bypass adjudication algorithm 452. Accordingly, medical device system 2 may store the episode data in memory for a physician to review.

In another example, if the change in the systolic pressure is 15 mmHg (or some other value less than the blood pressure threshold value), then processing circuitry 402 may not bypass adjudication algorithm 452, enabling adjudication algorithm 452 to determine the likelihood of the episode data being a true or false indication of a cardiac episode. In this way, the blood pressure condition may ensure that medical device system 2 stores episode data that occurs within a time window during which a change in blood pressure (e.g., systolic, diastolic, etc.) of the patient exceeds a blood pressure threshold value. This may be beneficial because the transmission of episode data within such a time window may be less likely to be a false indication of a cardiac episode, thus warranting review of the episode data by a physician. It should be understood that the above examples of processing circuitry 402 bypassing adjudication algorithm 452 based on blood pressure may be substantially similar to examples of processing circuitry 402 bypassing adjudication algorithm 452 based on PPT due to PPT being correlated with blood pressure.

In some examples, processing circuitry 402 may be configured to weigh each bypass condition of the set of bypass conditions to determine to bypass adjudication algorithm 452. In such an example, processing circuitry 402 may assign a weight (e.g., selected by a clinician, determined by an algorithm, such as a machine learning algorithm executed by processing circuitry 402, etc.) to each bypass condition of the set of bypass conditions, and, responsive to determining that the episode data satisfies one or more of the bypass conditions, calculate an aggregate weight of the one or more bypass conditions satisfied by the episode data. Processing circuitry 402 may then determine to bypass adjudication algorithm 452 based on the aggregate weight satisfying the weight threshold. For example, if the aggregate weight (e.g., 99%) exceeds a weight threshold value (e.g., 85%), then processing circuitry 402 may bypass adjudication algorithm 452, storing the episode data in memory for a physician to review.

The set of bypass conditions may additionally or alternatively include an ischemic stroke condition. Processing circuitry 402 may determine that the episode data satisfies the ischemic stroke condition when patient has previously experienced an ischemic stroke (e.g., a stroke of known origin, a cryptogenic stroke, etc.), the occurrence of which may be indicated by a user of system via a user interface or retrieved from electronic health records, and the episode data received by processing circuitry 402 is a first transmission of the episode data for the cardiac episode after an elapse of a time interval (e.g., 15 days). For example, if a transmission of episode data by IMD 10 to medical device system 2 is the first transmission of episode data after an elapse of a time interval of 15 days, then processing circuitry 402 may determine that the episode data satisfies the interval condition and bypass the adjudication algorithm. Accordingly, medical device system 2 may store the episode data in memory for a physician to review. If instead the transmission of episode data by IMD 10 to medical device system 2 is not the first transmission of episode data after an elapse of the time interval of 15 days or is a transmission of episode data before the elapse of the time interval of 15 days, then processing circuitry 402 may not bypass adjudication algorithm 452, enabling adjudication algorithm 452 to determine the likelihood of the episode data being a true or false indication of a cardiac episode.

The set of bypass conditions may additionally or alternatively include a clinician activation condition. Processing circuitry 402 may determine that the episode data satisfies the clinician activation condition when the clinician provides an input (e.g., actuation of a user interface) that causes processing circuitry 402 to bypass the algorithm for a bypass period. For example, following a clinically significant event, a clinician may program processing circuitry 402 to bypass adjudication algorithm 452 for the bypass period (e.g., the 3 days following the clinically significant event) such that any episode data transmitted during the bypass period is not adjudicated by the bypass algorithm and instead stored in memory for a physician to review. Additionally or alternatively, the clinician may program specific criteria thresholds and/or parameters for satisfying the bypass conditions and bypassing adjudication algorithm 452.

The set of bypass conditions may additionally or alternatively include a similarity condition. Processing circuitry 402 may determine that the episode data satisfies the similarity condition when processing circuitry 402 determines (e.g., using a machine learning algorithm) that the similarity between the episode data and previous episode data that was adjudicated (e.g., by a clinician) to be a cardiac episode exceeds a similarity threshold.

In some examples, the bypass conditions of the set of bypass conditions may depend on the medical condition of a patient. For example, for a patient who experiences crypto stroke, the set of bypass conditions may include the time period condition, the frailty condition, and the similarity condition. On the other hand, for a patient who experiences syncope, the set of bypass conditions may include the time interval condition, the clinician activation condition, and the blood pressure condition. It should be understood that these examples are for purposes of illustration and that other sets of bypass conditions are contemplated by this disclosure.

Moreover, it should be understood that any of the conditions described herein may be modified by a clinician to customize the bypassing of adjudication algorithm 452. For example, a clinician may select durations, intervals, thresholds, events, sensitivities, etc., to customize any of the bypass conditions to suit the preferences and/or objectives of the clinician. In some examples, computing system 24 may store the customized programming by the clinician and automatically customize the bypass conditions (e.g., for a new patient) based on clinician feedback.

In some examples, processing circuitry 402 may transmit an indication of the one or more bypass conditions that were satisfied to the clinician. Processing circuitry 402 may further transmit determinations of adjudication algorithm 452 (e.g., the likelihood of the episode data being a true or false indication of a cardiac episode) regarding the episode data that satisfied the bypass conditions. In this way, the clinician may compare the clinician's determinations regarding the episode data with those of adjudication algorithm 452 to evaluate the utility, accuracy, etc., of the one or more bypass conditions and/or adjudication algorithm.

Other example bypass conditions may include the following:

Bypass adjudication algorithm 452 using other conditions only if R-wave amplitude sensed by IMD 10 is above a threshold amplitude of microvolts (e.g., 300 microvolts).

Bypass adjudication algorithm 452 or require very high confidence for a certain period before/after a medical intervention or if patient not on a medication. For example, post ablation a physician wants to know if ablation is successful and may take patient off of anti-coagulation so need very high sensitivity. Likewise a high risk (e.g., stroke) patient not on anti-coagulation needs ultra high sensitivity.

Bypass adjudication algorithm 452 for any auto detected episode that is correlated to patient activated episode (the device definition is if the auto detection happens within 20 minutes prior to activation it is considered correlated). Prior analyses have demonstrated that correlated episodes have a high PPV to being a true auto episode.

Bypass adjudication algorithm 452 in tiered approach such that patients with a high risk of stroke (e.g., higher $CHA_2DS_2VASc$ scores) are bypassed more frequently than patients with low risk of stroke (e.g., low $CHA_2DS_2VASc$ scores). For example, bypass adjudication algorithm 452 every 1/30 episodes for patients with $CHA_2DS_2VASc$ scores of 0-1; bypass adjudication algorithm 452 every 1/15 episodes for patients with $CHA_2DS_2VASc$ scores of 2-4; do not bypass adjudication algorithm 452 for patients with $CHA_2DS_2VASc$ scores ≥5.

a. The above claim could be repeated for individual components of the $CHA_2DS_2VASc$ scores (congestive heart failure, hypertension, age, diabetes, prior stroke/TIA, vascular disease, female gender). For example, since older patients are more likely to have AF, adjudication algorithm 452 could be bypassed more frequently for older patients vs. younger patients.

Bypass adjudication algorithm 452 if AF episode corresponds temporally with a decrease in patient activity as measured by the device. This may indicate that the patient is feeling symptomatic and therefore may be more indicative of a true AF episode.

For patients with cryptogenic stroke, bypass adjudication algorithm 452 for all AF episode detections.

For heart failure (HF) population, bypass adjudication algorithm 452 if the patient is in high risk group (or in the few days when they first transition to high risk group). Any episode detections happening at that time may be of higher interest to clinicians.

For HF population, bypass adjudication algorithm 452 based one or more physiological parameters, such as respiration rate, fluid indicated by impedance or drop in heart rate variability (HRV), decrease in activity, new onset AF, rapid rate during AF, etc. As noted above, a clinician and/or an algorithm may customize the thresholds for any of the bypass conditions to accommodate the specific preferences of clinicians and the personalized needs of patients.

Bypass adjudication algorithm 452 for the first 3 detections occurring within 1 week after a hospitalization/clinic visit/dialysis/medication change.

Bypass adjudication algorithm 452 for the first 3 PVC detections after a premature ventricular contraction (PVC) ablation (because physicians might want to know if the patient is continuing to have PVCs after PVC ablation. Physicians may especially want to know the morphology of the PVC so that they can determine the site of origin for the PVC.

Bypass adjudication algorithm 452 for the first 2 ventricular arrhythmia episodes after QT prolongation or significant QT changes are detected in the previous 30 minutes (since QT changes could lead to polymorphic VT which could in turn lead to sudden cardiac death).

Bypass adjudication algorithm 452 for the first detection of a different PVC morphology by the device (Physician may want to know if the patient has polymorphic PVCs to determine the sites of PVC origin in the heart. It is undesirable for adjudication algorithm 452 to miss one of the PVC morphologies especially if it is rare and occurs only once in a month or so)

If the patient is found to be at high HF risk, then bypass adjudication algorithm 452 for the first 2 ventricular arrhythmia episode detections during the high risk period since HF patients are susceptible to ventricular arrhythmias which may lead to sudden cardiac arrest in these patients.

If a patient were recently hospitalized for antiarrhythmic drug titration or if the patient's medication dosage was changed, then the physician can program to bypass adjudication algorithm 452 for the first 3 ventricular arrhythmia episodes since certain drug dosages can cause arrhythmias and the physician may not want to miss these episodes.

If a sleep apnea algorithm detects more than 10 sleep apnea events in a night, then bypass adjudication algorithm 452 for the first 2 AF episodes in that patient during that day. The physician may want to know if frequent sleep apnea is causing arrhythmias in the patient.

Bypass adjudication algorithm 452 for ventricular arrhythmia episodes occurring within 1 hour of more than 10 sleep apnea episode detections. Frequent sleep apnea episodes can cause ventricular ectopic beats and non-sustained VT during sleep which makes the patient more susceptible to sudden cardiac death.

The physician can program the threshold to bypass adjudication algorithm 452 for arrhythmia detections occurring within 2 hours of more than 10 sleep apnea episode detections if the patient has heart failure or other risk factors.

Bypass adjudication algorithm 452 if the average ventricular (Av. V.) rate during AF>Threshold (threshold programmable by physician or a set threshold).

Bypass adjudication algorithm 452 for as long as the patient is in high HF risk (or) Bypass adjudication algorithm 452 only for the first cardiac episode during the period when the patient is at high HF risk. Physicians may want to tune treatment for HF after a high risk alert if AF occurs in the middle of it.

Bypass adjudication algorithm 452 for the first 3 arrhythmia detections if the patient is in high COPD risk. (bronchodilators may increase the risk of cardiac arrythmias, and the physicians may want to know if the patient experiences frequent arrhythmias)

Bypass adjudication algorithm 452 for first 3 arrhythmia detections occurring within 1 day if more than 5 sleep apnea events are detected. Sleep apnea can increase the relative risk of nocturnal paroxysmal AF and SVT.

Bypass adjudication algorithm 452 for an hour if patient exhibits an abnormal (e.g., nocturnal) breathing pattern.

It should be understood that the number of events (e.g., episode detections), time periods (e.g., number of seconds, minutes, days, etc.), and/or the like in the bypass conditions are representative and not intended to be limiting. Accordingly, other numbers of events, time periods, and/or the like are contemplated by this disclosure.

Figure 5:
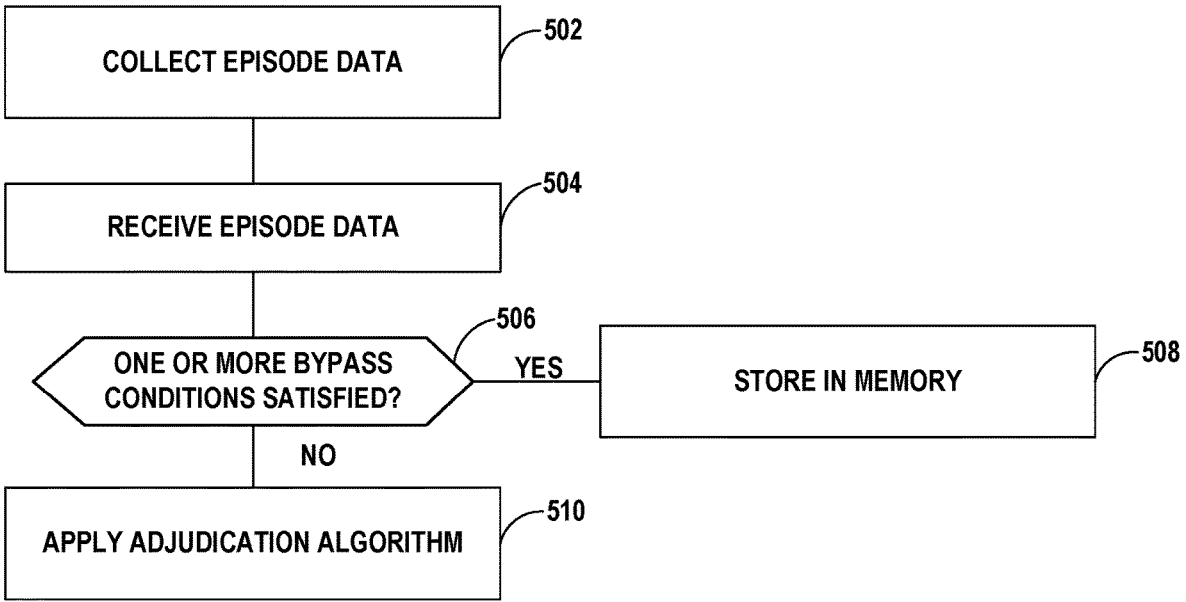
FIG. 5 is a flow diagram illustrating an example operation for utilizing an example medical device system.

FIG. 5 is an example technique for bypassing adjudication algorithm 452 in accordance with techniques of this disclosure. Although described herein primarily in the context of examples in which adjudication algorithm 452 and bypass module 454 are implemented by computing system 24, the techniques are not so limited. In some examples, the one or both of adjudication algorithm 452 and bypass module 454 may be implemented, in whole or part, by IMD 10 and/or external device 12.

According to the example of FIG. 5, IMD 10 may collect (e.g., via electrodes 16A, 16B) episode data indicative of electrical activity of a heart of patient 4 (502). For example, processing circuitry 50 may store the digitized cardiac EGM and features of the EGM used to detect the arrhythmia episode in memory 56 as episode data for the detected arrhythmia episode. In some examples, processing circuitry 50 stores one or more segments of the cardiac EGM data, features derived from the cardiac EGM data, and other episode data in response to instructions from external device 12 (e.g., when patient 4 experiences one or more symptoms of arrhythmia and inputs a command to external device 12 instructing IMD 10 to upload the data for analysis by a monitoring center or clinician).

Computing system 24 may receive episode data for episodes stored by medical devices, such as IMD 10, via communication circuitry 406 (504). For example, IMD 10 sends digitized cardiac EGM and other episode data to network 25 for processing by monitoring system 450 of FIG. 1. In some examples, processing circuitry 50 of IMD 10 transmits, via communication circuitry 54, the episode data for patient 4 to external device 12, which then transmits the episode data to computing system 24. The episode data may have been collected by the medical devices in response to the medical devices detecting arrhythmias and/or user input directing the storage of episode data.

Responsive to computing system 24 receiving the episode data, processing circuitry 402 of computing system may determine whether to bypass adjudication algorithm 452 based on the satisfaction of one or more bypass conditions of a set of bypass conditions (506). For example, responsive to one or more bypass conditions being satisfied (YES of 506), processing circuitry 402 may bypass adjudication algorithm 452, and processing circuitry 402 may store (e.g., in storage devices 408) the episode data as a true indication of a cardiac episode, such as an AF episode (508).

For example, if a transmission of episode data by IMD 10 to medical device system 2 is the first transmission of episode data during a time period of a particular month (e.g., May), then processing circuitry 402 may determine that the episode data satisfies the time period condition and bypass adjudication algorithm 452. Accordingly, processing circuitry 402 may store the episode data in memory (e.g., storage devices 408) for a physician to review. In another example, if the transmission of episode data is a subsequent transmission of episode data (e.g., a second transmission of episode data) during the time period, then processing circuitry 402 may not bypass adjudication algorithm 452.

In some examples, processing circuitry 402 may be configured to weigh each bypass condition of the set of bypass conditions (e.g., time period condition, frailty condition, implantation condition, etc.) to determine to bypass adjudication algorithm 452. In such an example, processing circuitry 402 may assign a weight to each bypass condition of the set of bypass conditions, and, responsive to determining that the episode data satisfies one or more of the bypass conditions, calculate an aggregate weight of the one or more bypass conditions satisfied by the episode data. Processing circuitry 402 may then determine to bypass adjudication algorithm 452 based on the aggregate weight satisfying the weight threshold. For example, if the aggregate weight (e.g., 99%) exceeds a weight threshold value (e.g., 85%), then processing circuitry 402 may bypass adjudication algorithm 452, storing the episode data in memory for a physician to review.

Responsive to processing circuitry 402 determining that no bypass condition is satisfied or that the aggregate weight does not satisfy the weight threshold (NO of 506), processing circuitry 402 may not bypass adjudication algorithm 452, and adjudication algorithm 452 may determine the likelihood of the episode data being a true or false indication of a cardiac episode (510). Adjudication algorithm 452 may output, for each of a plurality of arrhythmia type classifications, values indicative of the likelihood that an arrhythmia of the type occurred at any point during the episode. Monitoring system 450 may apply configurable thresholds (e.g., 50%, 75%, 90%, 95%, 99%) to the likelihood values to identify the episode as including one or more arrhythmia types, e.g., based on the likelihood for that classification meeting or exceeding the threshold.

In some examples, the techniques of the disclosure include a system that comprises means to perform any method described herein. In some examples, the techniques of the disclosure include a computer-readable medium comprising instructions that cause processing circuitry to perform any method described herein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module, unit, or circuit for purposes of clarity, it should be understood that the techniques of this disclosure may be performed by a combination of units, modules, or circuitry associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing circuitry" as used herein may refer to any of the foregoing structure or any other physical structure suitable for implementation of the described techniques. Also, the techniques could be fully implemented in one or more circuits or logic elements.

The following examples are illustrative of the techniques described herein.

Example 1: A method of monitoring a patient includes receiving, by processing circuitry of a medical device system, episode data for a cardiac episode; determining, by processing circuitry and based on satisfaction of one or more bypass conditions of a set of bypass conditions, to bypass an algorithm configured to determine a likelihood of the episode data being a false indication of the cardiac episode; and storing, by the processing circuitry and responsive to bypassing the algorithm, the episode data as a true indication of the cardiac episode.

Example 2: The method of example 1, wherein the set of bypass conditions includes a time period condition, and wherein the episode data satisfies the time period condition when the episode data received by the processing circuitry is a first transmission of episode data for the cardiac episode for a time period.

Example 3: The method of example 2, wherein a length of the time period is based on a health condition of the patient.

Example 4: The method of any of examples 1 through 3, wherein the set of bypass conditions includes an interval condition, and wherein the episode data satisfies the interval condition when the episode data received by the processing circuitry is a first transmission of episode data for the cardiac episode after an elapse of a time interval from a previous transmission of episode data for the cardiac episode.

Example 5: The method of any of examples 1 through 4, wherein the set of bypass conditions includes an implantation condition, and wherein the episode data satisfies the implantation condition when the episode data received by the processing circuitry is one of a first N transmissions of episode data for the cardiac episode after implantation of an implantable medical device of the medical device system.

Example 6: The method of example 5, wherein the first N transmissions includes a first ten transmissions of episode data for the cardiac episode after implantation of the implantable medical device.

Example 7: The method of any of examples 1 through 6, wherein the set of bypass conditions includes a long duration condition, and wherein the episode data satisfies the long duration condition when a duration of the episode data for the cardiac episode received by the processing circuitry exceeds a long duration threshold value.

Example 8: The method of any of examples 1 through 7, wherein the set of bypass conditions includes a short duration condition, and wherein the episode data satisfies the short duration condition when a duration of the episode data for the cardiac episode received by the processing circuitry is less than a short duration threshold value.

Example 9: The method of any of examples 1 through 8, wherein the set of bypass conditions includes a user input condition, and wherein the episode data satisfies the user input condition when the user provides a user input that causes the processing circuitry to bypass the algorithm for a bypass period.

Example 10: The method of any of examples 1 through 9, wherein the set of bypass conditions includes a frailty condition, and wherein the episode data satisfies the frailty condition when a transmission of episode data for the cardiac episode occurs within a time window during which the patient at least one of falls or exhibits body instability.

Example 11: The method of any of examples 1 through 10, wherein the set of bypass conditions includes a blood pressure condition, and wherein the episode data satisfies the blood pressure condition when a transmission of episode data for the cardiac episode occurs within a time window during which a change in blood pressure of the patient exceeds a blood pressure threshold value.

Example 12: The method of any of examples 1 through 11, wherein determining to bypass the algorithm includes: assigning a weight to each bypass condition of the set of bypass conditions, responsive to determining that the episode data satisfies one or more of the bypass conditions, calculating an aggregate weight of the one or more bypass conditions satisfied by the episode data, determining whether the aggregate weight exceeds a weight threshold value, and determining to bypass the algorithm based on the aggregate weight exceeding the weight threshold value.

Example 13: The method of example 12, wherein the weight assigned to each bypass condition is based on a health condition of the patient.

Example 14: The method of any of examples 1 through 13, further including storing, by the processing circuitry, an indication of why the processing circuitry determined to bypass the algorithm based on satisfaction of the one or more bypass conditions of the set of bypass conditions.

Example 15: A medical device system includes receive episode data for a cardiac episode; determine, based on satisfaction of one or more bypass conditions of a set of bypass conditions, whether to bypass an algorithm configured to determine a likelihood of the episode data being a false indication of the cardiac episode; and store, responsive to bypassing the algorithm, the episode data as a true indication of the cardiac episode.

Example 16: The medical device system of example 15, wherein the set of bypass conditions includes a time period condition, and wherein the episode data satisfies the time period condition when the episode data received by the processing circuitry is a first transmission of episode data for the cardia episode for a time period.

Example 17: The medical device system of example 16, wherein a length of the time period is based on a health condition of the patient.

Example 18: The medical device system of any of examples 15 through 17, wherein the set of bypass conditions includes an interval condition, and wherein the episode data satisfies the interval condition when the episode data received by the processing circuitry is a first transmission of episode data for the cardiac episode after an elapse of a time interval from a previous transmission of episode data for the cardiac episode.

Example 19: The medical device system of any of examples 15 through 18, wherein the set of bypass conditions includes an implantation condition, and wherein the episode data satisfies the implantation condition when the episode data received by the processing circuitry is one of a first N transmissions of episode data for the cardiac episode after implantation of an implantable medical device of the medical device system.

Example 20: The medical device system of example 19, wherein the first N transmissions includes a first ten transmissions of episode data for the cardiac episode after implantation of the implantable medical device.

Example 21: The medical device system of any of examples 15 through 20, wherein the set of bypass conditions includes a long duration condition, and wherein the episode data satisfies the long duration condition when a duration of the episode data for the cardiac episode received by the processing circuitry exceeds a long duration threshold value.

Example 22: The medical device system of any of examples 15 through 21, wherein the set of bypass conditions includes a short duration condition, and wherein the episode data satisfies the short duration condition when a duration of the episode data for the cardiac episode received by the processing circuitry is less than a short duration threshold value.

Example 23: The medical device system of any of examples 15 through 22, wherein the set of bypass conditions includes a user input condition, and wherein the episode data satisfies the user input condition when the user provides a user input that causes the processing circuitry to bypass the algorithm for a bypass period.

Example 24: The medical device system of any of examples 15 through 23, wherein the set of bypass conditions includes a frailty condition, and wherein the episode data satisfies the frailty condition when a transmission of episode data for the cardiac episode occurs within a time window during which the patient at least one of falls or exhibits body instability.

Example 25: The medical device system of any of examples 15 through 24, wherein the set of bypass conditions includes a blood pressure condition, and wherein the episode data satisfies the blood pressure condition when a transmission of episode data for the cardiac episode occurs within a time window during which a change in blood pressure of the patient exceeds a blood pressure threshold value.

Example 26: The medical device system of any of examples 15 through 25, wherein the processing circuitry is configured to determine to bypass the algorithm by: assigning a weight to each bypass condition of the set of bypass conditions, responsive to determining that the episode data satisfies one or more of the bypass conditions, calculating an aggregate weight of the one or more bypass conditions satisfied by the episode data, determining whether the aggregate weight exceeds a weight threshold value, and determining to bypass the algorithm based on the aggregate weight exceeding the weight threshold value.

Example 27: The medical device system of example 26, wherein the weight assigned to each bypass condition is based on a health condition of the patient.

Example 28: The medical device system of any of examples 15 through 27, wherein the processing circuitry is further configured to store an indication of why the processing circuitry determined to bypass the algorithm based on satisfaction of the one or more bypass conditions of the set of bypass conditions.

Example 29: A computer-readable medium includes receive episode data; determine, based on satisfaction of one or more bypass conditions of a set of bypass conditions, whether to bypass an algorithm configured to determine a likelihood of the episode data being a false indication of a cardiac episode; and store, responsive to bypassing the algorithm, the episode data as a true indication of the cardiac episode.

Various examples have been described. These and other examples are within the scope of the following claims.

What is claimed is:

1. A medical device system comprising processing circuitry configured to:

receive episode data for a cardiac episode, wherein the episode data comprises cardiac signal data and additional data;

determine, based on the additional data satisfying one or more bypass conditions of a set of bypass conditions, whether to bypass an algorithm configured for application to the cardiac signal data to determine a likelihood of the episode data being a false indication of the cardiac episode; and store, responsive to bypassing the algorithm, the episode data as a true indication of the cardiac episode.

2. The medical device system of claim 1, wherein the set of bypass conditions comprises a time period condition, and wherein the additional data satisfies the time period condition when the episode data received by the processing circuitry is a first transmission of episode data for the cardiac episode for a time period.

3. The medical device system of claim 2, wherein a length of the time period is based on a health condition of a patient.

4. The medical device system of claim 1, wherein the set of bypass conditions comprises an interval condition, and wherein the additional data satisfies the interval condition when the episode data received by the processing circuitry is a first transmission of episode data for the cardiac episode after an elapse of a time interval from a previous transmission of episode data for the cardiac episode.

5. The medical device system of claim 1, wherein the set of bypass conditions comprises an implantation condition, and wherein the additional data satisfies the implantation condition when the episode data received by the processing circuitry is one of a first N transmissions of episode data for the cardiac episode after implantation of an implantable medical device of the medical device system.

6. The medical device system of claim 5, wherein the first N transmissions comprises a first ten transmissions of episode data for the cardiac episode after implantation of the implantable medical device.

7. The medical device system of claim 1, wherein the set of bypass conditions comprises a long duration condition, and wherein the additional data satisfies the long duration condition when a duration of the cardiac signal data for the cardiac episode received by the processing circuitry exceeds a long duration threshold value.

8. The medical device system of claim 1, wherein the set of bypass conditions comprises a short duration condition, and wherein the additional data satisfies the short duration condition when a duration of the cardiac signal data for the cardiac episode received by the processing circuitry is less than a short duration threshold value.

9. The medical device system of claim 1, wherein the set of bypass conditions comprises a user input condition, and wherein the additional data satisfies the user input condition when a user provides a user input that causes the processing circuitry to bypass the algorithm for a bypass period.

10. The medical device system of claim 1, wherein the set of bypass conditions comprises a frailty condition, and wherein the additional data satisfies the frailty condition when a transmission of episode data for the cardiac episode occurs within a time window during which a patient at least one of falls or exhibits body instability.

11. The medical device system of claim 1, wherein the set of bypass conditions comprises a blood pressure condition, and wherein the episode additional data satisfies the blood pressure condition when a transmission of episode data for the cardiac episode occurs within a time window during which a change in blood pressure of a patient exceeds a blood pressure threshold value.

12. The medical device system of claim 1, wherein the processing circuitry is configured to determine to bypass the algorithm by:

assigning a weight to each bypass condition of the set of bypass conditions, responsive to determining that the additional data satisfies the one or more bypass conditions of the set of bypass conditions, calculating an aggregate weight of the one or more bypass conditions satisfied by the episode data, determining whether the aggregate weight exceeds a weight threshold value, and determining to bypass the algorithm based on the aggregate weight exceeding the weight threshold value.

13. The medical device system of claim 12, wherein the weight assigned to each bypass condition is based on a health condition of a patient.

14. The medical device system of claim 1, wherein the processing circuitry is further configured to store an indication of why the processing circuitry determined to bypass the algorithm based on satisfaction of the one or more bypass conditions of the set of bypass conditions.

15. A method of monitoring a patient, the method comprising:

receiving, by processing circuitry of a medical device system, episode data for a cardiac episode, wherein the episode data comprises cardiac signal data and additional data;

determining, by processing circuitry and based on the additional data satisfying one or more bypass conditions of a set of bypass conditions, to bypass an algorithm configured for application to the cardiac signal data to determine a likelihood of the episode data being a false indication of the cardiac episode; and storing, by the processing circuitry and responsive to bypassing the algorithm, the episode data as a true indication of the cardiac episode.

16. The method of claim 15, wherein the set of bypass conditions comprises a time period condition, and wherein the additional data satisfies the time period condition when the episode data received by the processing circuitry is a first transmission of episode data for the cardiac episode for a time period.

17. The method of claim 15, wherein the set of bypass conditions comprises an interval condition, and wherein the additional data satisfies the interval condition when the episode data received by the processing circuitry is a first transmission of episode data for the cardiac episode after an elapse of a time interval from a previous transmission of episode data for the cardiac episode.

18. The method of claim 15, wherein determining to bypass the algorithm comprises:

assigning a weight to each bypass condition of the set of bypass conditions, responsive to determining that the additional data satisfies the one or more bypass conditions of the set of bypass conditions, calculating an aggregate weight of the one or more bypass conditions satisfied by the episode data, determining whether the aggregate weight exceeds a weight threshold value, and determining to bypass the algorithm based on the aggregate weight exceeding the weight threshold value.

19. The method of claim 15, further comprising storing, by the processing circuitry, an indication of why the processing circuitry determined to bypass the algorithm based on satisfaction of the one or more bypass conditions of the set of bypass conditions.

20. A non-transitory computer-readable medium comprising instructions that, when executed, cause processing circuitry to:

receive episode data, wherein the episode data comprises cardiac signal data and additional data;

determine, based on the additional data satisfying one or more bypass conditions of a set of bypass conditions, whether to bypass an algorithm configured for application to the cardiac signal data to determine a likelihood of the episode data being a false indication of a cardiac episode; and store, responsive to bypassing the algorithm, the episode data as a true indication of the cardiac episode.

\* \* \* \* \*